(12) United States Patent
Li et al.

(10) Patent No.: US 9,371,327 B2
(45) Date of Patent: Jun. 21, 2016

(54) PDE1 INHIBITOR COMPOUNDS

(75) Inventors: Peng Li, New York, NY (US); Jun Zhao, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 120 days.

(21) Appl. No.: 13/701,225

(22) PCT Filed: May 31, 2011

(86) PCT No.: PCT/US2011/038541
§ 371 (c)(1),
(2), (4) Date: Mar. 18, 2013

(87) PCT Pub. No.: WO2011/153135
PCT Pub. Date: Dec. 8, 2011

(65) Prior Publication Data
US 2013/0324565 A1   Dec. 5, 2013

Related U.S. Application Data

(60) Provisional application No. 61/349,957, filed on May 31, 2010.

(51) Int. Cl.
| | | |
|---|---|---|
| A01N 43/90 | (2006.01) |
| A61K 31/519 | (2006.01) |
| C07D 487/00 | (2006.01) |
| C07D 487/04 | (2006.01) |
| A61K 31/5575 | (2006.01) |
| A61K 45/06 | (2006.01) |
| A61K 31/165 | (2006.01) |

(52) U.S. Cl.
CPC ............ *C07D 487/04* (2013.01); *A61K 31/165* (2013.01); *A61K 31/519* (2013.01); *A61K 31/5575* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,689,863 A | 9/1972 | Matsuoka et al. |
| 3,993,650 A | 11/1976 | Tarzia et al. |
| 4,663,326 A | 5/1987 | Hamilton et al. |
| 4,824,848 A | 4/1989 | Naka et al. |
| 5,202,328 A | 4/1993 | De Laszlo et al. |
| 5,223,501 A | 6/1993 | Chakravarty et al. |
| 5,294,612 A | 3/1994 | Bacon et al. |
| 5,393,755 A | 2/1995 | Neustadt et al. |
| 5,409,934 A | 4/1995 | Smith et al. |
| 5,719,283 A | 2/1998 | Bell et al. |
| 5,939,419 A | 8/1999 | Tulshlan |
| 6,133,273 A | 10/2000 | Gilbert et al. |
| 6,166,019 A | 12/2000 | Meyer et al. |
| 6,235,742 B1 | 5/2001 | Bell et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,756,373 B1 | 6/2004 | Allerton et al. |
| 7,153,824 B2 | 12/2006 | Palmer et al. |
| 7,157,451 B2 | 1/2007 | Atwal et al. |
| 7,247,639 B2 | 7/2007 | Wilson et al. |
| 8,858,911 B2 | 10/2014 | Li et al. |
| 9,006,258 B2 | 4/2015 | Fienberg et al. |
| 2003/0092908 A1 | 5/2003 | Pitts et al. |
| 2003/0162782 A1 | 8/2003 | Grossman et al. |
| 2004/0254183 A1 | 12/2004 | Basarab et al. |
| 2005/0048573 A1 | 3/2005 | Artis et al. |
| 2005/0075795 A1 | 4/2005 | Pandit |
| 2005/0113379 A1 | 5/2005 | Ge et al. |
| 2006/0160831 A1 | 7/2006 | Tsutsumi et al. |
| 2006/0252790 A1 | 11/2006 | Allen et al. |
| 2007/0208029 A1 | 9/2007 | Barlow et al. |
| 2008/0176961 A1 | 7/2008 | Greengard et al. |
| 2008/0188492 A1 | 8/2008 | Li et al. |
| 2008/0194592 A1 | 8/2008 | Mates et al. |
| 2009/0137549 A1 | 5/2009 | Edward et al. |
| 2010/0087450 A1 | 4/2010 | Fienberg et al. |
| 2010/0173878 A1 | 7/2010 | Li et al. |
| 2010/0273753 A1 | 10/2010 | Li et al. |
| 2010/0273754 A1 | 10/2010 | Li et al. |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li et al. |
| 2013/0085123 A1 | 4/2013 | Li et al. |
| 2013/0331363 A1 | 12/2013 | Li et al. |
| 2013/0338124 A1 | 12/2013 | Li et al. |
| 2014/0315868 A1 | 10/2014 | Li et al. |
| 2015/0119370 A1 | 4/2015 | Li et al. |
| 2015/0197524 A1 | 7/2015 | Li et al. |
| 2015/0353556 A1 | 12/2015 | Li et al. |

FOREIGN PATENT DOCUMENTS

| | | |
|---|---|---|
| DE | 19709126 | 3/1997 |
| DE | 19931206 | 1/2001 |

(Continued)

OTHER PUBLICATIONS

Ahn, H., et al. "Potent Tetracyclic Guanine Inhibitors of PDE1 and PDE5 Cyclic Guanosine Monophosphate Phosphodiesterases with Oral Antihypertensive Activity", J. Med. Chem. (1997) 40(14):2196-2210.

(Continued)

*Primary Examiner* — Jeffrey H Murray
(74) *Attorney, Agent, or Firm* — Hoxie & Associates LLC

(57) ABSTRACT

The present invention relates to optionally substituted (5- or 7-oxy)-3,4-dihydro-(optionally 4-oxo, 4-thioxo or 4-imino)-1H-pyrrolo[3,4-d]pyrimidin-2(3H,6H)-ones, e.g., Compounds of Formula II-A' or II-B' as described herein, processes for their production, their use as pharmaceuticals and pharmaceutical compositions comprising them.

17 Claims, No Drawings

(56) References Cited

FOREIGN PATENT DOCUMENTS

| | | |
|---|---|---|
| EP | 0063381 | 4/1982 |
| EP | 0166054 | 1/1986 |
| EP | 0201188 | 12/1986 |
| EP | 0237289 | 9/1987 |
| EP | 0306185 | 8/1988 |
| EP | 0353941 | 7/1989 |
| EP | 0383465 | 2/1990 |
| EP | 0636626 | 2/1995 |
| EP | 1097706 | 11/2000 |
| EP | 0911333 | 4/2002 |
| EP | 1852108 | 11/2007 |
| JP | 53031694 | 3/1978 |
| JP | 63-010788 | 1/1988 |
| JP | 01265027 | 4/1988 |
| JP | 02289518 | 11/1990 |
| KR | 10-1991-0006866 | 9/1991 |
| NL | 1186466 | 7/1962 |
| WO | WO 91/19717 | 12/1991 |
| WO | WO 96/28429 | 9/1996 |
| WO | WO 97/05138 | 2/1997 |
| WO | WO 97/30710 | 8/1997 |
| WO | WO 98/28301 | 7/1998 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/020724 | 3/2003 |
| WO | WO 03/037899 | 5/2003 |
| WO | WO 2004/018474 | 3/2004 |
| WO | WO 2004/056831 | 7/2004 |
| WO | WO 2004/087906 | 10/2004 |
| WO | WO 2006/133261 | 12/2006 |
| WO | WO 2007/025103 | 3/2007 |
| WO | WO 2007/031977 | 3/2007 |
| WO | WO 2007/143568 | 12/2007 |
| WO | WO 2007/143705 | 12/2007 |
| WO | WO 2008/063505 | 5/2008 |
| WO | WO 2009/022007 | 2/2009 |
| WO | WO 2009/073210 | 6/2009 |
| WO | WO 2009/075784 | 6/2009 |
| WO | WO 2009/131974 | 10/2009 |
| WO | WO 2010/065147 | 6/2010 |
| WO | WO 2011/153129 | 12/2011 |
| WO | WO 2011/153136 | 12/2011 |
| WO | WO 2011/153138 | 12/2011 |
| WO | WO 2012/171016 | 12/2012 |

OTHER PUBLICATIONS

Al-Afaleq, E., et al., "Heterocyclic o-Aminonitriles: Preparation of Pyrazolo[3,4-d]-pyrimidines with Modification of the substituents at the 1-position", *Molecules*, 6, pp. 621-638, (2001).
Banker, Gilbert S. et al., Modem Pharmaceutics, Marcel Dekker, New York, 1996.
Bender et al., "Cyclic Nucleotide Phosphodiesterases: Molecular Regulation to Clinical Use" PharmcoL Rev., 2006, 58, pp. 488-520.
Fienberg et al., "DARPP-32: Regulator of the Efficacy of Dopaminergic Neurotransmission", Science, (1998) 281, pp. 838-842.
Gelbin, et al., "Ketene-S, N-acetals as synthons for heterocycles new synthesis of pyrimidinones", *Journal Fuer Praktische Chemie*, vol. 329, No. 5, pp. 753-766, (1987).
Gilbert, A., et al., "Pyrazolopyrimidine-2,4-dione Sulfonamides: Novel and Selective Calcitonin Inducers," J. Med. Chem., (2002), 45: pp. 2342-2345.
Goodman & Gilman, The Pharmacological Basis of Therapeutics, McGraw-Hill Interamericana. 2007, p. 892. (cited within text of Office Action from corresponding Costa Rican application, attached herein).
Greengard et al., "Beyond the Dopamine Receptor: the DARPP-32lProtein Phosphatase-1 Cascade", Neuron, 1999,23, pp. 435,447.

Lugnier, et al., *Pharmacology & Therapeutics*, 2006, 109, pp. 306-398.
Lundqvist et al., Exploitation of Structural and Regulatory Diversity in Glutamate Racemases, Nature (2007) 447:817-822.
Mani, S.K. et al., "Requirement for DARPP-32 in Progesterone-Facilitated Sexual Receptivity in Female Rats and Mice", Science, 2000, 287, pp. 1053-1056.
Medina. Frontiers in Neuroscience, 2011, 5, pp. 21.
Morgan, Expert Opinion, 2006, 11 (3), 403-417.
Murray et al., "Expression and activity of cAMP phosphodiesterase isoforms in pulmonary artery smooth muscle cells from patients with pulmonary hypertension: role for PDE1", Am. J. Physiol. Lunr:I Cell Mol. Physiol. 2007, 292, pp. L294-L303.
Nishi, et al., *J. Neurosci* (1997) 17: 8147-8155.
Noguchi, M., et al., "A Facile Preparation of 7-(Substituted amino)-6 H-pyrrolo[3,7- d]-pyrimidine Derivativesl)", Bulletin of the Chemical Society of Japan, vol. 62, pp. 3043-3045, (Jan. 1, 1989).
Poulsen et al.Hlgh-Pressure Synthesis of Enantiomerlcally Pure C-6 Substituted Pyrazolo[3,4-d]pyrimidines Biorganic & Medicinal Chemistry letter (2001) 11:191-193.
Reed et al., "Phosphodiesterase 1 B Knock-Out Mice Exhibit Exaggerated Locomotor Hyperactivity and DARPP-32 Phosphorylation in Response to Dopamine Agonists and Display Impaired Spatial Learning", The Joumal of Neuroscience, 2002, 22(12), pp. 5188-5197.
Rybalkin et al., "Cyclic GMP Phosphodiesterases and Regulation of Smooth Muscle Function", Circ. Res. 2003,93, pp. 280-291.
Turko et al., Inhibition of Cyclic GMP-Binding Cyclic GMP-Specific Phosphodiesterase (Type 5) by Sildenafil and Related Compounds Molecular Pharmacology (1990) 56:124-130.
Wolff, Manfred E., Burger's Medicinal Chemistry and Drug Discovery, Fifth Ed., vol. 1: Principles and Practice, John Wiley & Sons, 1995, 975.
Xia, et al., Synthesis and Evaluation of Polycyclic Pyrazolo[3,4-d]pyrimidines as PDE1 and PDE5 cGMP Phosphodiesterase Inhibitors, J. Med. Chem., 40, 4372-77 (1997).
Park, et al., "Traumatic Brain Injury: Can the consequences be stopped?" CMAJ, 178(9), 1163-1170, (2008).
Wermuth, CG, ed., "Molecular Variations based on isosteric replacements" The Practice of Chemistry, Technomics, Inc., vol. 1, Section 13, pp. 235-271 (Aug. 15, 1998) Japanese Translated Version.
Miller, "Targeting Cyclic Nucleotide Phosphodiesterase in the Heart: Therapeutic Implications" J. of Cardiovasc. Trans. Res., 9 pages (2010).
Mokni et al., "Concerted Regulation of cGMP and cAMP Phosphodiesterases in Early Cardiac Hypertrophy Induced by Angiotensin II" PLOS One, 5(12): e14227, 28 pages (2010).
Tominaga et al., "Synthesis of pyrazolo [3,4-d]pyrimidine derivatives using ketene dithioacetals" Journal of Heterocyclic Chemistry, 27(3), 775-83 (1990).
Bibliographic Data and Abstract of JP 63010788(A) provided by Espacenet, Publication Date: Jan. 18, 1988, Date Accessed: Jan. 28, 2016.
Bibliographic Data of JP S5331694 provided by Espacenet, Publication Date: Mar. 25, 1978, Date Accessed: Jan. 28, 2016.
Boyd et al., "Dopamine Receptor Signaling and Current and Future Antipsychotic Drugs", Current Antipsychotics, Handbook of Experimental Pharmacology, 212:53-86 (2012).
Ehrman et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice", Genes, Brain, and Behavior, 5:540-551 (2006).
Fienberg, "The DARPP-32 Knockout Mouse", Brain Res. Rev. 3:313-319 (2000).
Gilbert et al., "Novel and Selective Calcitonin-Inducing Agents", Journal of Medicinal Chemistry, 43(6): 1223-1233 (2000).
Girault et al., "The Neurobiology of Dopamine Signaling", Arch Neurol, 61(5): 641-4 (2004).
Kakkar et al., "Inhibition of Bovine Brain Calmodulin-Dependent Cyclic Nucleotide Phosphodiesterase Isozymes by Deprenyl", Life Sciences, 59(21): 337-341 (1996).

(56) References Cited

OTHER PUBLICATIONS

Kakkar et al., "Amantadine: an antiparkinsonian agent inhibits bovine brain 60 kDa calmodulin-dependent cyclic nucleotide phosphodiesterase isozyme", Brain Res. 749(2):290-294 (1997).

Kakkar et al., "Calmodulin-dependent cyclic nucleotide phosphodiesterase (PDE1)", Cell Mol Life Sci. 55(8-9):1164-1186 (1999).

Keravis et al., "Cyclic Nucleotide Phosphodiesterase (ODE) Isozymes as Targets of the Intracellular Signaling Network: Benefits of Pde Inhibitors in Various Diseases and Perspectives for Future Therapeutic Developments", British Journal of Pharmacology, 165: 1288-1305 (2012).

Registry No. 353484-98-7, Registry (STN) [on-line], Entered STN: Aug. 29, 2001, Retrieved on Jan. 31, 2014.

Office Actions for U.S. Appl. No. 12/303,618, filed Dec. 5, 2008.

US 9,371,327 B2

PDE1 INHIBITOR COMPOUNDS

CROSS REFERENCE TO RELATED APPLICATIONS

This application is a United States Application under 35 U.S.C. §371 claiming benefit of PCT Application No. PCT/US2011/038541, filed on May 31, 2011, which claims priority from U.S. Provisional Application No. 61/349,957, filed on May 31, 2010, the contents of each of which are hereby incorporated by reference in their entirety.

TECHNICAL FIELD

The present invention relates to optionally substituted (5- or 7-oxy)-3,4-dihydro-(optionally 4-oxo, 4-thioxo or 4-imino)-1H-pyrrolo[3,4-d]pyrimidin-2(3H,6H)-ones, preferably a compound of Formula II-A or II-B as described below, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression, narcolepsy, damage to cognitive function, e.g., in schizophrenia, or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyms, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1A or PDE1B activity.

SUMMARY OF THE INVENTION

The invention provides optionally substituted (5- or 7-oxy)-3,4-dihydro-(optionally 4-oxo, 4-thioxo or 4-imino)-1H-pyrrolo[3,4-d]pyrimidin-2(3H,6H)-ones, preferably a Compound of Formula II, e.g., II-A and II-B:

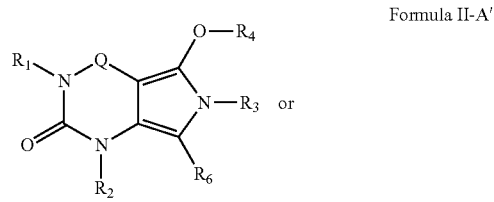

Formula II-A'

-continued

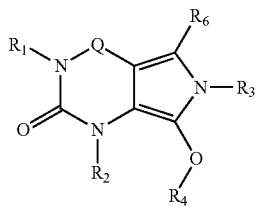

Formula II-B' wherein
(i) Q is —C(=S)—, —C(=O)—, —C(=N($R_7$))— or —C($R_{14}$)($R_{15}$)—;
(ii) $R_1$ is H or $C_{1-6}$alkyl (e.g., methyl or ethyl);
(iii) $R_2$ is
  H,
  $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, $R_2$ may be a trifluoromethyl or 2,2,2-trifluoroethyl,
  N($R_{14}$)($R_{15}$)—$C_{1-6}$alkyl (e.g., 2-(dimethylamino)ethyl or 2-aminopropyl),
  aryl$C_{0-6}$alkyl (e.g., phenyl or benzyl),
  heteroaryl$C_{0-6}$alkyl (e.g., pyridinylmethyl),
  $C_{1-6}$alkoxyaryl$C_{1-6}$alkyl (e.g., 4-methoxybenzyl);
  -G-J wherein:
    G is a single bond or, alkylene (e.g., methylene);
    J is cycloalkyl or heterocycloalkyl (e.g., oxetan-2-yl, pyrolyin-3-yl, pyrolyin-2-yl) optionally substituted with one or more $C_{1-6}$alkyl (e.g., (1-methylpyrrolidin-2-yl)), amino (e.g., —NH$_2$),
    for example, -G-J may be —$C_{0-4}$alkyl-$C_{3-8}$cycloalkyl (e.g., cyclopentyl, cyclohexyl or cyclopropylmethyl) optionally substituted with one or more $C_{1-6}$alkyl, amino (e.g., —NH$_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);
(iv) $R_3$ is
  1) -D-E-F wherein:
    D is a single bond, $C_{1-6}$alkylene (e.g., methylene), or arylalkylene (e.g., p-benzylene or —CH$_2$C$_6$H$_4$—);
    E is
      a single bond,
      $C_{1-4}$alkylene (e.g., methylene)
      $C_{2-6}$alkynylene (e.g., ethynylene, prop-2-yn-1-ylene), ethynylene, prop-2-yn-1-ylene),
      —$C_{0-4}$alkylarylene (e.g., phenylene or —C$_6$H$_4$—, -benzylene- or —CH$_2$C$_6$H$_4$—), wherein the arylene group is optionally substituted with halo (e.g., Cl or F),
      heteroarylene (e.g., pyridinylene or pyrimidinylene),
      amino$C_{1-6}$alkylene (e.g., —CH$_2$N(H)—),
      amino (e.g., —N(H)—);
      $C_{3-8}$cycloalkylene optionally containing one or more heteroatom selected from N or O (e.g., piperidinylene), F is
      H,
      halo (e.g., F, Br, Cl),
      $C_{1-6}$alkyl (e.g., isopropyl or isobutyl),
      $C_{1-6}$alkoxy (e.g., methoxy),
      halo$C_{1-6}$alkyl (e.g., trifluoromethyl),
      aryl (e.g., phenyl),
      $C_{3-8}$cycloalkyl optionally containing at least one atom selected from a group consisting of N or O (e.g., cyclopentyl, cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
      heteroaryl, for example pyridyl, (e.g., pyrid-2-yl), pyrimidinyl (for example, pyrimidin-2-yl), thiadiazolyl (e.g., 1,2,3-thiadiazol-4-yl), diazolyl (e.g., pyrazolyl (for example, pyrazol-1-yl) or imidazolyl (e.g., imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with $C_{1-6}$alkyl, halo (e.g., fluoro) or halo$C_{1-6}$alkyl, for example, 6-fluoropyrid-2-yl;
      amino (e.g., —NH$_2$),
      $C_{1-6}$alkoxy,
      —O-halo$C_{1-6}$alkyl (e.g., —O—CF$_3$),
      $C_{1-6}$alkylsulfonyl (for example, methylsulfonyl or —S(O)$_2$CH$_3$),
      —C(O)—$R_{13}$,
      —N($R_{14}$)($R_{15}$); or
  2) a substituted heteroarylalkyl, e.g., substituted with haloalkyl; or
  3) attached to the nitrogen on the pyrrolo portion of Formula II-A or II-B and is a moiety of Formula A

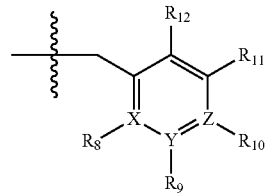

Formula A wherein X, Y and Z are, independently, N or C, and $R_8$, $R_9$, $R_{11}$ and $R_{12}$ are independently H or halogen (e.g., Cl or F); and $R_{10}$ is
  halogen,
  $C_{1-6}$alkyl,
  $C_{1-6}$alkoxy (e.g., methoxy),
  $C_{3-8}$cycloalkyl,
  hetero$C_{3-8}$cycloalkyl (e.g., pyrrolidinyl)
  halo$C_{1-6}$alkyl (e.g., trifluoromethyl),
  aryl (e.g., phenyl),
  heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl),
  $C_{1-6}$alkyl sulfonyl (e.g., methyl sulfonyl), arylcarbonyl (e.g., benzoyl),
heteroarylcarbonyl,
alkoxycarbonyl, (e.g., methoxycarbonyl),
aminocarbonyl;
  wherein the aryl, heteroaryl, cycloalkyl or heterocloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl)
  preferably $R_{10}$ is phenyl, pyridyl, e.g., 2-pyridyl, pyrrolidinyl optionally substituted with halo (e.g., F) or $C_{1-6}$alkyl (e.g., methyl);
  provided that when X, Y or X is nitrogen, $R_8$, $R_9$ or $R_{10}$, respectively, is not present;
(v) $R_4$ is:
  $C_{1-4}$alkyl (e.g., isopropyl),
  $C_{3-7}$cycloalkyl (e.g., cyclopentyl or cyclohexyl),
  aryl (e.g., phenyl),
  $C_{3-7}$cycloalkyl (e.g., cyclopentyl),
  heteroaryl (e.g., pyridyl, for example, pyrid-4-yl), or
  aryl$C_{1-4}$alkyl (e.g., benzyl),
    wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl,
(vi) $R_6$ is H, $C_{1-6}$alkyl (e.g., methyl), hydroxy, $C_{1-6}$alkoxy, aryloxy, —N($R_{16}$)($R_{17}$), oxo (e.g., =O), or $C_{3-8}$cycloalkyl;
(vii) $R_7$ is H, $C_{1-6}$alkyl (e.g., methyl) or $C_{3-8}$cycloalkyl wherein said cycloalkyl is optionally substituted with one or more oxo (e.g., 2,5-dioxopyrrolidin-1-yl);
(viii) $R_{13}$ is —N($R_{14}$)($R_{15}$), $C_{1-6}$alkyl (e.g., methyl), —O$C_{1-6}$alkyl (e.g., —OCH$_3$), halo$C_{1-6}$alkyl (trifluoromethyl), aryl (e.g., phenyl), or heteroaryl; and
(ix) $R_{14}$ and $R_{15}$ are independently H or $C_{1-6}$alkyl;
(x) $R_{16}$ and $R_{17}$ are independently H, $C_{1-6}$alkyl, aryl (e.g., phenyl), heteroaryl, wherein said aryl or heteroaryl is optionally substituted with halo (e.g., fluoro), $C_{1-6}$alkoxy (e.g. methoxy);
in free or salt form.

The invention further provides a Compound of II-A' and II-B', wherein said compound is a compound of Formula II-A or II-B:

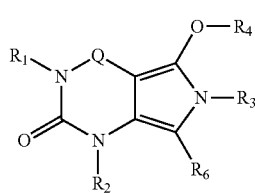

Formula II-A

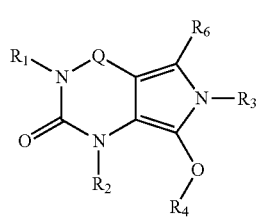

Formula II-B wherein all substituents are previously defined in Formula II-A' and II-B' except that $R_4$ is selected from $C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl), or
aryl$C_{1-4}$alkyl (e.g., benzyl),
  wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl, In still another embodiment, the invention provides a compound of Formula II-A or II-B as follows:

2.1 Formula II-A or II-B, wherein Q is —C(=S)—, —C(=O)—, —C(=N($R_7$))— or —C($R_{14}$)($R_{15}$);
2.2 Formula II-A or II-B, wherein Q is —C(=S)—;
2.3 Formula II-A or II-B, wherein Q is —C(=O);
2.4 Formula II-A or II-B, wherein Q is —C(=N($R_7$))— or —C($R_{14}$)($R_{15}$)—;
2.5 Formula II-A or II-B, or any of 2.1-2.4, wherein $R_1$ is H or $C_{1-6}$alkyl (e.g., methyl or ethyl);
2.6 Formula II-A or II-B, or any of 2.1-2.4, wherein $R_1$ is methyl or ethyl;
2.7 Formula II-A or II-B, or any of 2.1-2.6, wherein $R_2$ is
  H,
  $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, $R_2$ may be a trifluoromethyl or 2,2,2-trifluoroethyl,
  N($R_{14}$)($R_{15}$)—$C_{1-6}$alkyl (e.g., 2-(dimethylamino)ethyl or 2-aminopropyl),
  aryl$C_{0-6}$alkyl (e.g., phenyl or benzyl),
  heteroaryl$C_{0-6}$alkyl (e.g., pyridinylmethyl),
  $C_{1-6}$alkoxyaryl$C_{1-6}$alkyl (e.g., 4-methoxybenzyl);
  -G-J wherein:
    G is a single bond or, alkylene (e.g., methylene);
    J is cycloalkyl or heterocycloalkyl (e.g., oxetan-2-yl, pyrolyin-3-yl, pyrolyin-2-yl) optionally substituted with one or more $C_{1-6}$alkyl (e.g., (1-methylpyrrolidin-2-yl)), amino (e.g., —NH$_2$),
    for example, -G-J may be —$C_{0-4}$alkyl-$C_{3-8}$cycloalkyl (e.g., cyclopentyl, cyclohexyl or cyclopropylmethyl) optionally substituted with one or more $C_{1-6}$alkyl, amino (e.g., —NH$_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);
2.8 Formula II-A or II-B, or any of 2.1-2.7, wherein $R_2$ is $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, $R_2$ may be a trifluoromethyl or 2,2,2-trifluoroethyl;
2.9 Formula II-A or II-B, or any of 2.1-2.7, wherein $R_2$ is $C_{1-6}$alkyl (isopropyl, isobutyl, 2-methylbutyl, 2,2-dimethylpropyl;
2.10 Formula II-A or II-B, or any of 2.1-2.7, wherein $R_2$ is isobutyl;
2.11 Formula II-A or II-B, or any of 2.1-2.10, wherein $R_3$ is 1) -D-E-F wherein:

D is a single bond, $C_{1-6}$alkylene (e.g., methylene), or arylalkylene (e.g., p-benzylene or —$CH_2C_6H_4$—);

E is
a single bond,
$C_{1-4}$alkylene (e.g., methylene)
$C_{2-6}$alkynylene (e.g., ethynylene, prop-2-yn-1-ylene), ethynylene, prop-2-yn-1-ylene),
—$C_{0-4}$alkylarylene (e.g., phenylene or —$C_6H_4$—, -benzylene- or —$CH_2C_6H_4$—), wherein the arylene group is optionally substituted with halo (e.g., Cl or F),
heteroarylene (e.g., pyridinylene or pyrimidinylene),
amino$C_{1-6}$alkylene (e.g., —$CH_2N(H)$—),
amino (e.g., —$N(H)$—);
$C_{3-8}$cycloalkylene optionally containing one or more heteroatom selected from N or O (e.g., piperidinylene), F is
H,
halo (e.g., F, Br, Cl),
$C_{1-6}$alkyl (e.g., isopropyl or isobutyl),
$C_{1-6}$alkoxy (e.g., methoxy),
halo$C_{1-6}$alkyl (e.g., trifluoromethyl),
aryl (e.g., phenyl),
$C_{3-8}$cycloalkyl optionally containing at least one atom selected from a group consisting of N or O (e.g., cyclopentyl, cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
heteroaryl, for example pyridyl, (e.g., pyrid-2-yl), pyrimidinyl (for example, pyrimidin-2-yl), thiadiazolyl (e.g., 1,2,3-thiadiazol-4-yl), diazolyl (e.g., pyrazolyl (for example, pyrazol-1-yl) or imidazolyl (e.g., imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with $C_{1-6}$alkyl, halo (e.g., fluoro) or halo$C_{1-6}$alkyl, for example, 6-fluoropyrid-2-yl;
amino (e.g., —$NH_2$),
$C_{1-6}$alkoxy,
—O-halo$C_{1-6}$alkyl (e.g., —O—$CF_3$),
$C_{1-6}$alkylsulfonyl (for example, methylsulfonyl or —$S(O)_2CH_3$),
—$C(O)$—$R_{13}$,
—$N(R_{14})(R_{15})$; or 2) a substituted heteroarylalkyl, e.g., substituted with haloalkyl; or 3) attached to the nitrogen on the pyrrolo portion of Formula II-A or II-B and is a moiety of Formula A

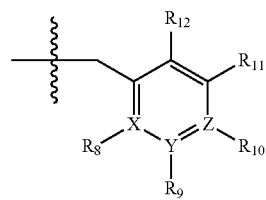

Formula A wherein X, Y and Z are, independently, N or C, and $R_8$, $R_9$, $R_{11}$ and $R_{12}$ are independently H or halogen (e.g., Cl or F); and $R_{10}$ is
halogen,
$C_{1-6}$alkyl,
$C_{1-6}$alkoxy (e.g., methoxy),
$C_{3-8}$cycloalkyl,
hetero$C_{3-8}$cycloalkyl (e.g., pyrrolidinyl or piperidinyl),
halo$C_{1-6}$alkyl (e.g., trifluoromethyl),
aryl (e.g., phenyl),
heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl),
$C_{1-6}$alkyl sulfonyl (e.g., methyl sulfonyl),
arylcarbonyl (e.g., benzoyl),
heteroarylcarbonyl,
alkoxycarbonyl, (e.g., methoxycarbonyl),
aminocarbonyl;
wherein the aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl)
preferably $R_{10}$ is phenyl, pyridyl, e.g., 2-pyridyl, pyrrolidinyl optionally substituted with halo (e.g., F) or $C_{1-6}$alkyl (e.g., methyl);
provided that when X, Y or X is nitrogen, $R_8$, $R_9$ or $R_{10}$, respectively, is not present;

2.12 Formula II-A or II-B, or any of 2.1-2.10, wherein $R_3$ is attached to the nitrogen on the pyrrolo portion of Formula II-A or II-B and is a moiety of Formula A

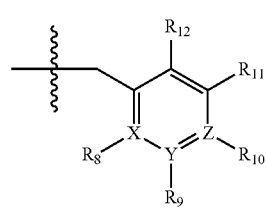

Formula A wherein X, Y and Z are, independently, N or C, and $R_8$, $R_9$, $R_{11}$ and $R_{12}$ are independently H or halogen (e.g., Cl or F); and $R_{10}$ is
halogen,
$C_{1-6}$alkyl,
$C_{1-6}$alkoxy (e.g., methoxy),
$C_{3-8}$cycloalkyl, heteroC$_{3-8}$cycloalkyl (e.g., pyrrolidinyl or piperidinyl),
haloC$_{1-6}$alkyl (e.g., trifluoromethyl),
aryl (e.g., phenyl),
heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl),
C$_{1-6}$alkyl sulfonyl (e.g., methyl sulfonyl),
arylcarbonyl (e.g., benzoyl),
heteroarylcarbonyl,
alkoxycarbonyl, (e.g., methoxycarbonyl),
aminocarbonyl;
wherein the aryl, heteroaryl, cycloalkyl or heterocycloalkyl is optionally substituted with one or more C$_{1-6}$alkyl (e.g., methyl), halogen (e.g., chloro or fluoro), haloC$_{1-6}$alkyl (e.g., trifluoromethyl), hydroxy, carboxy, —SH, or an additional aryl or heteroaryl (e.g., biphenyl or pyridylphenyl)
preferably R$_{10}$ is phenyl, pyridyl, e.g., 2-pyridyl, pyrrolidinyl optionally substituted with halo (e.g., F) or C$_{1-6}$alkyl (e.g., methyl);
provided that when X, Y or X is nitrogen, R$_8$, R$_9$ or R$_{10}$, respectively, is not present;

2.13 Formula II-A or II-B, or any of 2.1-2.10, wherein R$_3$ is attached to the nitrogen on the pyrrolo portion of Formula II-A or II-B and is a moiety of Formula A

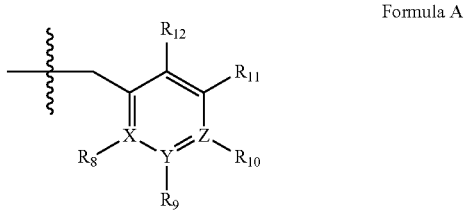

Formula A wherein X, Y and Z are, independently, N or C, and R$_8$, R$_9$, R$_{11}$ and R$_{12}$ are independently H or halogen (e.g., Cl or F); and R$_{10}$ is
C$_{1-6}$alkoxy (e.g., methoxy),
C$_{3-8}$cycloalkyl,
heteroC$_{3-8}$cycloalkyl (e.g., pyrrolidinyl or piperidinyl)
haloC$_{1-6}$alkyl (e.g., trifluoromethyl),
aryl (e.g., phenyl),
heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl),
wherein the aryl, heteroaryl, cycloalkyl or heterocycloalkyl is optionally substituted with one or more C$_{1-6}$alkyl (e.g., methyl), halogen (e.g., chloro or fluoro), haloC$_{1-6}$alkyl (e.g., trifluoromethyl), hydroxy, carboxy, —SH, or an additional aryl or heteroaryl (e.g., biphenyl or pyridylphenyl)
preferably preferably R$_{10}$ is phenyl, pyridyl, e.g., 2-pyridyl, pyrrolidinyl optionally substituted with halo (e.g., F) or C$_{1-6}$alkyl (e.g., methyl);
provided that when X, Y or X is nitrogen, R$_8$, R$_9$ or R$_{10}$, respectively, is not present;

2.14 Formula II-A or II-B, or any of 2.1-2.13, wherein R$_4$ is:
C$_{1-4}$alkyl (e.g., isopropyl),
C$_{3-7}$cycloalkyl (e.g., cyclopentyl or cyclohexyl),
aryl (e.g., phenyl),
heteroaryl (e.g., pyridyl, for example, pyrid-4-yl), or
arylC$_{1-4}$alkyl (e.g., benzyl),
wherein the aryl or heteroaryl is optionally substituted with one or more group selected from halo (e.g., F, Cl), hydroxy, C$_{1-6}$alkyl, C$_{1-6}$alkoxy and C$_{3-8}$cycloalkyl, for example, R$_6$ is 3-chlorophenyl or 4-fluorophenyl, 2.15 Formula II-A or II-B, or any of 2.1-2.14, wherein R$_4$ is aryl (e.g., phenyl) optionally substituted with halo (e.g., 4-fluorophenyl), hydroxy (e.g., 4-hydroxyphenyl), C$_{1-6}$alkyl, C$_{1-6}$alkoxy or another aryl group (e.g., biphenyl-4-ylmethyl);

2.16 Formula II-A or II-B, or any of 2.1-2.14, wherein R$_4$ is aryl (e.g., phenyl) optionally substituted with halo (e.g., 4-fluorophenyl);

2.17 Formula II-A or II-B, or any of 2.1-2.16, wherein R$_6$ is H, C$_{1-6}$alkyl (e.g., methyl), hydroxy, C$_{1-6}$alkoxy, aryloxy, —N(R$_{16}$)(R$_{17}$), oxo (e.g., =O), or C$_{3-8}$cycloalkyl;

2.18 Formula II-A or II-B, or any of 2.1-2.16, wherein R$_6$ is H;

2.19 Formula II-A or II-B, or any of 2.1-2.18, wherein R$_7$ is H, C$_{1-6}$alkyl (e.g., methyl) or C$_{3-8}$cycloalkyl wherein said cycloalkyl is optionally substituted with one or more oxo (e.g., 2,5-dioxopyrrolidin-1-yl);

2.20 Formula II-A or II-B, or any of 2.1-2.18, wherein R$_7$ is H or C$_{1-6}$alkyl (e.g., methyl);

2.21 Formula II-A or II-B, or any of 2.1-2.18, wherein R$_7$ is H;

2.22 Formula II-A or II-B, or any of 2.1-2.21, wherein R$_{14}$ and R$_{15}$ are independently H or C$_{1-6}$alkyl;

2.23 Formula II-A or II-B, or any of 2.1-2.22, wherein R$_{16}$ and R$_{17}$ are independently H, C$_{1-6}$alkyl, aryl (e.g., phenyl), heteroaryl, wherein said aryl or heteroaryl is optionally substituted with halo (e.g., fluoro), C$_{1-6}$alkoxy (e.g., methoxy);

2.24 Formula II-A or II-B, or any of 2.1-2.22, wherein R$_{16}$ is H and R$_{17}$ is aryl (phenyl) wherein said aryl or heteroaryl is optionally substituted with halo (e.g., fluoro), C$_{1-6}$alkoxy (e.g., methoxy), 2.25 any of the preceding formulae wherein the compound is selected from any of the following:

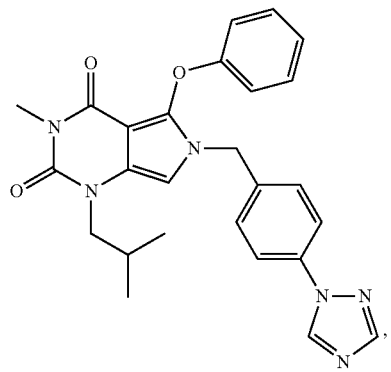

-continued

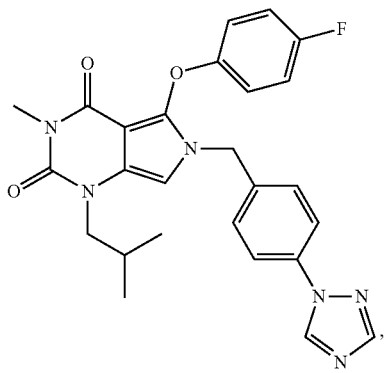

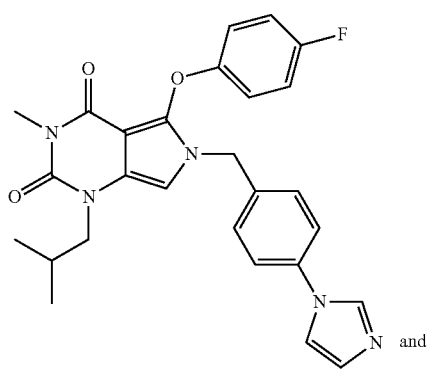 and

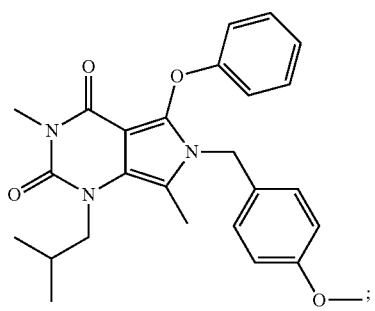

2.26 any of the preceding formulae wherein the compound is further selected from any of the following:

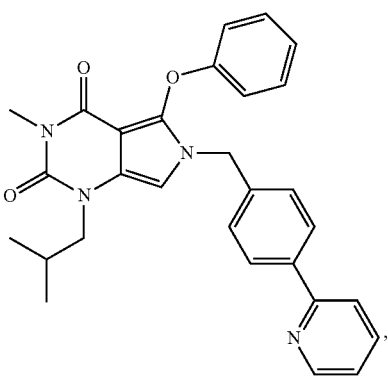

-continued

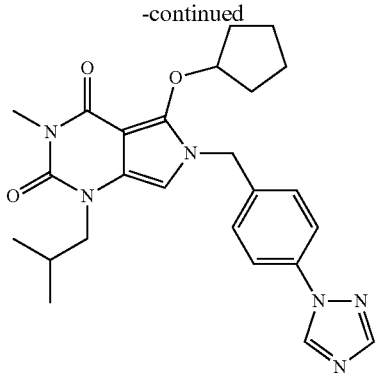

2.27 any of the preceding formulae wherein the compounds inhibit phosphodiesterase-mediated (e.g., PDE1-mediated, especially PDE1A-mediated or PDE1B-mediated) hydrolysis of cGMP, e.g., with an $IC_{50}$ of less than 10 μM, preferably less than 1 μM, more preferably less than 500 nM, preferably less than 100 nM in an immobilized-metal affinity particle reagent PDE assay, for example, as described in Example 7, in free or salt form.

In a particular embodiment, the Compound of Formula II-A or II-B, is a Compound of Formula III-A or III-B, wherein (i) Q is —C(=S)—, —C(=O)—, —C(=N($R_7$))— or —C($R_{14}$)($R_{15}$)—;

(ii) $R_1$ is H or $C_{1-6}$alkyl (e.g., methyl);

(iii) $R_2$ is
  H,
  $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, $R_2$ may be a trifluoromethyl or 2,2,2-trifluoroethyl,
  N($R_{14}$)($R_{15}$)—$C_{1-6}$alkyl (e.g., 2-(dimethylamino)ethyl or 2-aminopropyl),
  aryl$C_{0-6}$alkyl (e.g., phenyl or benzyl),
  heteroaryl$C_{0-6}$alkyl (e.g., pyridinylmethyl),
  $C_{1-6}$alkoxyaryl$C_{1-6}$alkyl (e.g., 4-methoxybenzyl);
  -G-J wherein:
    G is a single bond or, alkylene (e.g., methylene);
    J is cycloalkyl or heterocycloalkyl (e.g., oxetan-2-yl, pyrolyin-3-yl, pyrolyin-2-yl) optionally substituted with one or more $C_{1-6}$alkyl (e.g., (1-methylpyrrolidin-2-yl)), amino (e.g., —$NH_2$),
    for example, -G-J may be —$C_{0-4}$alkyl-$C_{3-8}$cycloalkyl (e.g., cyclopentyl, cyclohexyl or cyclopropylmethyl) optionally substituted with one or more $C_{1-6}$alkyl, amino (e.g., —$NH_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);

(iv) $R_3$ is:
  (a) -D-E-F wherein:
    D is $C_{1-6}$alkylene (e.g., methylene);
    E is —$C_0$alkylarylene (e.g., phenylene),
    F is
      halo (e.g., F, Br, Cl),
      $C_{1-6}$alkyl (e.g., isopropyl or isobutyl), $C_{1-6}$alkoxy (e.g., methoxy),
haloC$_{1-6}$alkyl (e.g., trifluoromethyl),
aryl (e.g., phenyl),
$C_{3-8}$cycloalkyl optionally containing at least one atom selected from a group consisting of N or O (e.g., cyclopentyl, cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
heteroaryl, for example pyridyl, (e.g., pyrid-2-yl), pyrimidinyl (for example, pyrimidin-2-yl), thiadiazolyl (e.g., 1,2,3-thiadiazol-4-yl), diazolyl (e.g., pyrazolyl (for example, pyrazol-1-yl) or imidazolyl (e.g., imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with $C_{1-6}$alkyl, halo (e.g., fluoro) or haloC$_{1-6}$alkyl, for example, 6-fluoropyrid-2-yl;
amino (e.g., —NH$_2$),
$C_{1-6}$alkoxy,
—O-haloC$_{1-6}$alkyl (e.g., —O—CF$_3$),
$C_{1-6}$alkylsulfonyl (for example, methylsulfonyl or —S(O)$_2$CH$_3$),
—C(O)—R$_{13}$,
—N(R$_{14}$)(R$_{15}$); or
(b) a substituted heteroarylalkyl, e.g., substituted with haloalkyl; or
(c) attached to the nitrogen on the pyrrolo portion of Formula III-A or III-B and is a moiety of Formula A

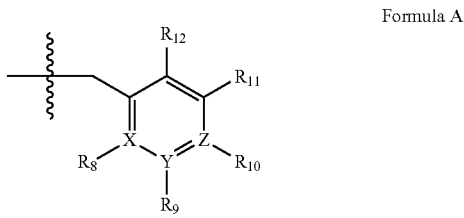

Formula A wherein X, Y and Z are, independently, N or C, and R$_8$, R$_9$, R$_{11}$ and R$_{12}$ are independently H or halogen (e.g., Cl or F); and R$_{10}$ is
halogen,
$C_{1-6}$alkyl,
$C_{1-6}$alkoxy (e.g., methoxy),
$C_{3-8}$cycloalkyl,
heteroC$_{3-8}$cycloalkyl (e.g., pyrrolidinyl)
haloC$_{1-6}$alkyl (e.g., trifluoromethyl),
aryl (e.g., phenyl),
heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl),
$C_{1-6}$alkyl sulfonyl (e.g., methyl sulfonyl),
arylcarbonyl (e.g., benzoyl),
heteroarylcarbonyl,
alkoxycarbonyl, (e.g., methoxycarbonyl),
aminocarbonyl;
wherein the aryl, heteroaryl, cycloalkyl or heterocycloalkyl is optionally substituted with one or more $C_{1-6}$alkyl (e.g., methyl), halogen (e.g., chloro or fluoro), haloC$_{1-6}$alkyl (e.g., trifluoromethyl), hydroxy, carboxy, —SH, or an additional aryl or heteroaryl (e.g., biphenyl or pyridylphenyl)
preferably R$_{10}$ is phenyl, pyridyl, e.g., 2-pyridyl, pyrrolidinyl optionally substituted with halo (e.g., F) or $C_{1-6}$alkyl (e.g., methyl);
provided that when X, Y or X is nitrogen, R$_8$, R$_9$ or R$_{10}$, respectively, is not present
(v) R$_4$ is
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl), or
arylC$_{1-4}$alkyl (e.g., benzyl),
wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, R$_6$ is 3-chlorophenyl or 4-fluorophenyl,
(vi) R$_6$ is H, $C_{1-6}$alkyl (e.g., methyl) or $C_{3-8}$cycloalkyl;
(vii) R$_{13}$ is —N(R$_{14}$)(R$_{15}$), $C_{1-6}$alkyl (e.g., methyl), —OC$_{1-6}$alkyl (e.g., —OCH$_3$), haloC$_{1-6}$alkyl (trifluoromethyl), aryl (e.g., phenyl), or heteroaryl; and
(viii) R$_{14}$ and R$_{15}$ are independently H or $C_{1-6}$alkyl, in free or salt form.

In still another embodiment, the Compound of Formula II-A or II-B is a Compound of Formula IV-A or IV-B, wherein:
(i) Q is —C(=S)—, —C(=O)—, —C(=N(R$_7$))— or —C(R$_{14}$)(R$_{15}$)—;
(ii) R$_1$ is H or $C_{1-6}$alkyl (e.g., methyl);
(iii) R$_2$ is
$C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, R$_2$ may be a trifluoromethyl or 2,2,2-trifluoroethyl,
(iv) R$_3$ is:
(a) -D-E-F wherein:
D is $C_{1-6}$alkylene (e.g., methylene);
E is —C$_0$alkylarylene (e.g., phenylene),
F is
$C_{1-6}$alkoxy (e.g., methoxy),
aryl (e.g., phenyl),
$C_{3-8}$cycloalkyl optionally containing at least one atom selected from a group consisting of N or O (e.g., cyclopentyl, cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
heteroaryl, for example pyridyl, (e.g., pyrid-2-yl), pyrimidinyl (for example, pyrimidin-2-yl), thiadiazolyl (e.g., 1,2,3-thiadiazol-4-yl), diazolyl (e.g., pyrazolyl (for example, pyrazol-1-yl) or imidazolyl (e.g., imidazol-1-yl, 4-methylimidazolyl, 1-methylimidazol-2-yl), triazolyl (e.g., 1,2,4-triazol-1-yl), tetrazolyl (e.g., tetrazol-5- yl), alkoxadiazolyl (e.g., 5-methyl-1,2,4-oxadiazol), pyrazolyl (e.g., pyrazol-1-yl), wherein said heteroaryl is optionally substituted with $C_{1-6}$alkyl, halo (e.g., fluoro) or halo$C_{1-6}$alkyl, for example, 6-fluoropyrid-2-yl; or (b) $R_3$ is attached to the nitrogen on the pyrrolo portion of Formula IV-A or IV-B and is a moiety of Formula A

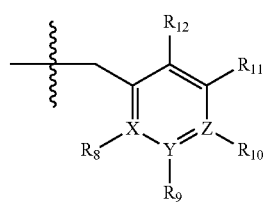

Formula A wherein X, Y and Z are, independently, N or C, and $R_8$, $R_9$, $R_{11}$ and $R_{12}$ are independently H or halogen (e.g., Cl or F); and $R_{10}$ is
$C_{1-6}$alkoxy (e.g., methoxy),
$C_{3-8}$cycloalkyl,
hetero$C_{3-8}$cycloalkyl (e.g., pyrrolidinyl)
aryl (e.g., phenyl),
heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl),
wherein the aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl)
preferably $R_{10}$ is phenyl, pyridyl, e.g., 2-pyridyl, pyrrolidinyl optionally substituted with halo (e.g., F) or $C_{1-6}$alkyl (e.g., methyl);
provided that when X, Y or X is nitrogen, $R_8$, $R_9$ or $R_{10}$, respectively, is not present (v) $R_4$ is
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl), or
aryl$C_{1-4}$alkyl (e.g., benzyl),
wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl,
(vi) $R_6$ is H, $C_{1-6}$alkyl (e.g., methyl) or $C_{3-8}$cycloalkyl;
(vii) $R_{14}$ and $R_{15}$ are independently H or $C_{1-6}$alkyl,
in free or salt form.

In still another embodiment, the Compound of Formula II-A or II-B is a Compound of Formula V-A or V-B, wherein:
(i) Q is —C(═O)—;
(ii) $R_1$ is H or $C_{1-6}$alkyl (e.g., methyl);
(iii) $R_2$ is $C_{1-6}$alkyl (e.g., isopropyl, isobutyl, 2-methylbutyl, 2,2-dimethylpropyl);

(iv) $R_3$ is:
(c) -D-E-F wherein:
D is $C_{1-6}$alkylene (e.g., methylene);
E is —$C_0$alkylarylene (e.g., phenylene),
F is selected form methoxy, pyridyl, (e.g., pyrid-2-yl), thiadiazolyl (e.g., 1,2,3-thiadiazol-4-yl), diazolyl (e.g., pyrazolyl (for example, pyrazol-1-yl) or imidazolyl (e.g., imidazol-1-yl, 4-methylimidazolyl, 1-methylimidazol-2-yl), triazolyl (e.g., 1,2,4-triazol-1-yl), 6-fluoropyrid-2-yl, 1-methylpyrrolidin-2-yl; or
(d) $R_3$ is attached to the nitrogen on the pyrrolo portion of Formula V-A or V-B and is a moiety of Formula A

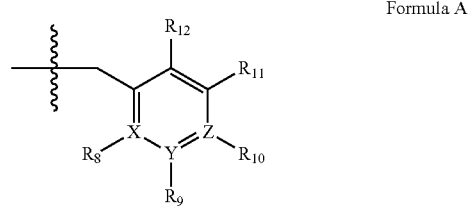

Formula A wherein X, Y and Z are, independently, N or C, and $R_8$, $R_9$, $R_{11}$ and $R_{12}$ are independently H or halogen (e.g., Cl or F); and $R_{10}$ is selected form methoxy, pyridyl, (for example, pyrid-2-yl), 6-fluoropyrid-2-yl, diazolyl (e.g., imidazolyl or pyrazolyl), triazolyl (e.g., 1,2,4-triazol-1-yl), 1-methylpyrroldin-2-yl;
provided that when X, Y or X is nitrogen, $R_8$, $R_9$ or $R_{10}$, respectively, is not present (v) $R_4$ is
$C_{1-4}$alkyl (e.g., isopropyl),
$C_{3-7}$cycloalkyl (e.g., cyclopentyl or cyclohexyl),
aryl (e.g., phenyl),
heteroaryl (e.g., pyridyl, for example, pyrid-4-yl), or
aryl$C_{1-4}$alkyl (e.g., benzyl),
wherein the aryl or heteroaryl is optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl,
(vi) $R_6$ is H, $C_{1-6}$alkyl (e.g., methyl) or $C_{3-8}$cycloalkyl,
in free or salt form.

In still another embodiment, the Compound of Formula II-A or II-B is a Compound of Formula VI-A or VI-B, wherein:
(i) Q is —C(═O)—;
(ii) $R_1$ is H or $C_{1-6}$alkyl (e.g., methyl);
(iii) $R_2$ is $C_{1-6}$alkyl (e.g., isopropyl, isobutyl, 2-methylbutyl, 2,2-dimethylpropyl);
(iv) $R_3$ is:
(a) -D-E-F wherein:
D is $C_{1-6}$alkylene (e.g., methylene);
E is —$C_0$alkylarylene (e.g., phenylene),
F is selected form methoxy, pyridyl, (e.g., pyrid-2-yl), thiadiazolyl (e.g., 1,2,3-thiadiazol-4-yl), diazolyl (e.g., pyrazolyl (for example, pyrazol-1-yl) or imidazolyl (e.g., imidazol-1-yl, 4-methylimidazolyl, 1-methylimidazol-2-yl), triazolyl (e.g., 1,2,4-triazol-1-yl), 6-fluoropyrid-2-yl, 1-methylpyrrolidin-2-yl; or
(b) $R_3$ is attached to the nitrogen on the pyrrolo portion of Formula VI-A or VI-B and is a moiety of Formula A

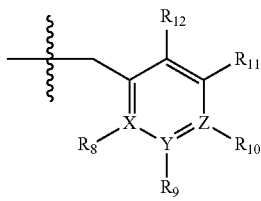
Formula A wherein X, Y and Z are, independently, N or C, and $R_8$, $R_9$, $R_{11}$ and $R_{12}$ are independently H or halogen (e.g., Cl or F); and $R_{10}$ is selected form methoxy, pyridyl, (for example, pyrid-2-yl), 6-fluoropyrid-2-yl, diazolyl (e.g., imidazolyl or pyrazolyl), triazolyl (e.g., 1,2,4-triazol-1-yl), 1-methylpyrroldin-2-yl;

provided that when X, Y or X is nitrogen, $R_8$, $R_9$ or $R_{10}$, respectively, is not present (v) $R_4$ is
aryl (e.g., phenyl) optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl, (vi) $R_6$ is H,
in free or salt form.

In yet another embodiment, the compound of the invention, e.g., any one of the Compound of Formula II-A' or II-B', Formulae II-A or II-B to VI-A or VI-B, or any of formulae 2.1-2.27, is a compound of Formula VII-A or VII-B, wherein:
Q is —C(=O)—;
$R_2$ is $C_{1-6}$alkyl (e.g., isopropyl, isobutyl, 2-methylbutyl, 2,2-dimethylpropyl), preferably isobutyl;
$R_3$ is:
-D-E-F, wherein D is methyl, E is aryl (e.g., phenyl), and F is $C_{1-6}$alkoxy (e.g., methoxy) or heteroaryl (e.g., heteroaryl, for example pyridyl, (e.g., pyrid-2-yl), diazolyl (e.g., imidazolyl), or triazolyl (e.g., 1,2,4-triazol-1-yl); or
attached to the nitrogen on the pyrrolo portion of any of Formulae II-A or II-B to VI-A or VI-B and is a moiety of Formula A

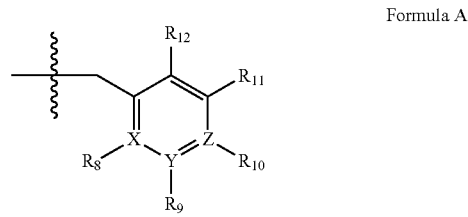
Formula A wherein X, Y and Z are C; $R_8$, $R_9$, $R_{11}$ and $R_{12}$ are H; and $R_{10}$ is $C_{1-6}$alkoxy (e.g., methoxy) or heteroaryl, for example pyridyl, (e.g., pyrid-2-yl), diazolyl (e.g., imidazolyl), or triazolyl (e.g., 1,2,4-triazol-1-yl);

$R_4$ is:
$C_{3-7}$cycloalkyl (e.g., cyclopentyl),
aryl (e.g., phenyl) optionally substituted with one or more group selected from halo (e.g., F, Cl), hydroxy, $C_{1-6}$alkyl, $C_{1-6}$alkoxy and $C_{3-8}$cycloalkyl, for example, $R_6$ is 3-chlorophenyl or 4-fluorophenyl,
$R_6$ is H or $C_{1-6}$alkyl (e.g., methyl),
in free or salt form.

In still another embodiment, the compound of the invention, e.g., any one of the Compound of Formula II-A' or II-B', Formulae II-A or II-B to VI-A or VI-B, or any of formulae 2.1-2.27 disclosed above, wherein said compound is a compound of Formula VIII-A or VIII-B, wherein
Q is —C(=O)—;
$R_2$ is $C_{1-6}$alkyl (e.g., isopropyl, isobutyl, 2-methylbutyl, 2,2-dimethylpropyl), preferably isobutyl;
$R_3$ is:
-D-E-F, wherein D is methyl, E is aryl (e.g., phenyl), and F is $C_{1-6}$alkoxy (e.g., methoxy) or heteroaryl (e.g., heteroaryl, for example pyridyl, (e.g., pyrid-2-yl), diazolyl (e.g., imidazolyl), or triazolyl (e.g., 1,2,4-triazol-1-yl); or
attached to the nitrogen on the pyrrolo portion of any of Formulae II-A or II-B to VI-A or VI-B and is a moiety of Formula A Formula A wherein X, Y and Z are C; $R_8$, $R_9$, $R_{11}$ and $R_{12}$ are H; and $R_{10}$ is $C_{1-6}$alkoxy (e.g., methoxy) or heteroaryl, for example pyridyl, (e.g., pyrid-2-yl), diazolyl (e.g., imidazolyl), or triazolyl (e.g., 1,2,4-triazol-1-yl);

$R_4$ is aryl (e.g., phenyl) optionally substituted with one or more halo (e.g., F), for example, $R_6$ is 4-fluorophenyl; and
$R_6$ is H or $C_{1-6}$alkyl (e.g., methyl),
in free or salt form.

In still another embodiment, the compound of the invention, e.g., any one of the Compound of Formula II-A' or II-B', Formulae II-A or II-B to VIII-A or VIII-B, or any of formulae 2.1-2.27 disclosed above, is a compound wherein F or $R_{10}$ is selected from 5-fluoropyrid-2-yl, 4-fluoropyrid-2-yl, 3-fluoropyrid-2-yl, 1-methylpyrrolidin-3-yl, 1-methylpyrrolidin-2-yl, 1-ethylpiperidin-1-yl or 1-methylpiperidin-2-yl, in free or salt form.

If not otherwise specified or clear from context, the following terms herein have the following meanings:
(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.
(b) "Cycloalkyl" as used herein is a saturated or unsaturated nonaromatic hydrocarbon moiety, preferably saturated, preferably comprising three to eight carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(c) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) Wherein E is phenylene, the numbering is as follows:

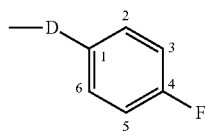

(g) It is intended that wherein the substituents end in "ene", for example, alkylene, phenylene or arylalkylene, said substitutents are intended to bridge or be connected to two other substituents. Therefore, methylene is intended to be —$CH_2$— and phenylene intended to be —$C_6H_4$— and arylalkylene is intended to be —$C_6H_4$—$CH_2$— or —$CH_2$—$C_6H_4$—.

(h) For ease of reference, the atoms on the pyrolo-pyrimidine core of the Compounds of the Invention are numbered in accordance with the numbering depicted below, unless otherwise noted.

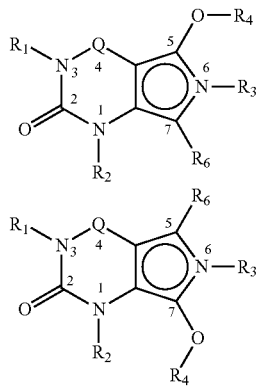

Compounds of the Invention may exist in free or salt form, e.g., as acid addition salts. In this specification unless otherwise indicated, language such as "Compounds of the Invention" is to be understood as embracing the compounds e.g., Compound of Formula II, e.g., Formula II-A' or II-B', Formulae II-A or II-B, e.g., any of 2.1-2.27, or any of III-A, III-B, IV-A, IV-B, V-A, V-B, VI-A or VI-B, VII-A or VII-B, or VIII-A or VIII-B in any form, for example, in free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included. In a particular embodiment, the salt of the compounds of the invention is a formic acid addition salt.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, for example, Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, for example, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

The invention also provides methods of making the Compounds of the Invention and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, cognitive impairment of schizophrenia, narcolepsy and diseases that may be alleviated by the enhancement of progesterone-signaling such as female sexual dysfunction), or a disease or disorder such as psychosis or glaucoma). This list is not intended to be exhaustive and may include other diseases and disorders as set forth below.

In another embodiment, the invention further provides a pharmaceutical composition comprising a Compound of the Invention, e.g., a Compound of Formula II-A' or II-B', Formula II-A or II-B, e.g., any of 2.1-2.27, or any of III-A, III-B, IV-A, IV-B, V-A, V-B, VI-A, VI-B, VII-A, VII-B, VIII-A or VIII-B in free or pharmaceutically acceptable salt form, in admixture with a pharmaceutically acceptable carrier.

DETAILED DESCRIPTION OF THE INVENTION

Methods of Making Compounds of the Invention

The Compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds. In particular, the intermediates and starting materials for the Compounds of the Invention may be prepared by methods and processes as described in PCT/US2009/06437. All references cited herein are hereby incorporated by reference in their entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

As will be appreciated by those skilled in the art, the Compounds of the Invention may exhibit keto-enol tautomerization. Therefore, the invention as defined in the present invention is to be understood as embracing both the structures as set forth herewith and their tautomeric forms.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-raradioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species, e.g., I, C and F respectively. Another example of useful isotope of the compound of the invention is the $^{11}C$ isotope. These radio isotopes are useful for radio-imaging and/or pharmacokinetic studies of the compounds of the invention. Methods of making isotopes of PDE1 inhibitors disclosed in WO 2011/043816, the contents of which are incorporated by reference in their entirety, may be used for making the isotopes of the compounds of the current invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and Abbreviations:
BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
K$_2$CO$_3$=potassium carbonate,
LiHMDS=lithium bis(trimethylsilyl)amide,
LDA=lithium diisopropylamide
MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid,
THF=tetrahedrofuran.

The synthetic methods in this invention are illustrated below. The significances for the R groups are as set forth above for Formula II-A' or II-B', Formula II-A or II-B unless otherwise indicated.

In an aspect of the invention, compounds II-A and II-B may be formed by reacting a compound of 1-A and 1-B respectively with for example a R$_3$-L in a solvent such as DMF and a base such as K$_2$CO$_3$ or cesium carbonate at room temperature or with heating:

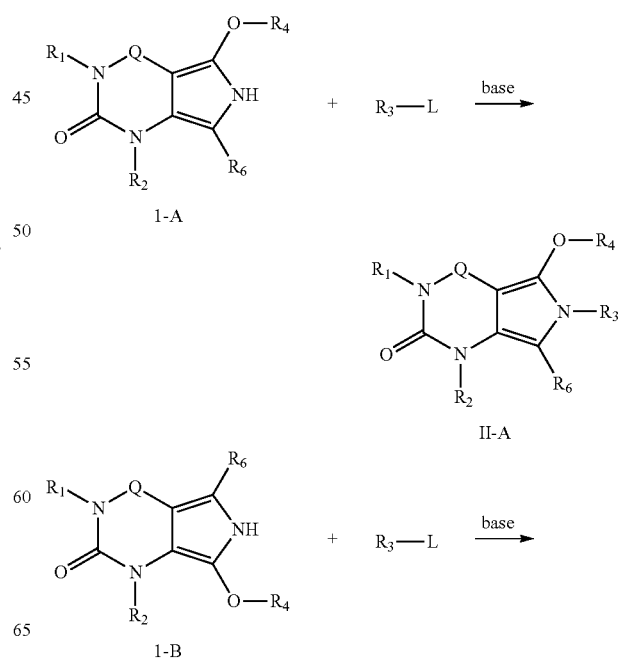

-continued

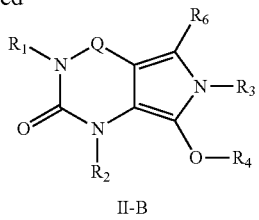
II-B wherein all the substitutents are as defined previously; L is a leaving group such as a halogen, mesylate, or tosylate.

Alternatively, compounds II-A and II-B may be synthesized by reacting a compound of 1-C and 1-D respectively with for example a R$_4$OH in a solvent such as dioxane and a base such as cesium carbonate or in neat condition with heating.

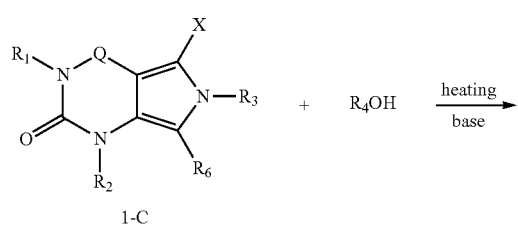

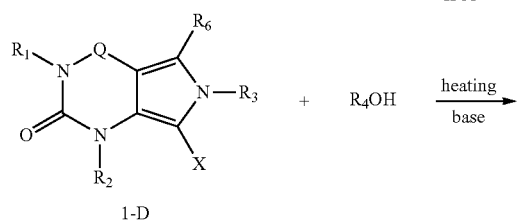

wherein all the substitutents are as defined previously; X is a leaving group such as a halogen group.

Compound 1-C, e.g., wherein Q is C(═O) and X is a chloro group, may be prepared by, e.g., reacting compound 1-G with a chlorinating reagent such as hexachloroethane in the presence of a strong base or lithium reagent such as LiHMDS. Compound 1-D, e.g., wherein Q is C(═O) and X is a chloro group, may be prepared by, e.g., reacting compound 1-H with a chlorinating reagent such NCS in a solvent such as CCl$_4$. Sometimes, R$_3$ can be a protective group such as a para-methoxybenzyl (PMB) group. Under this circumstance, compound 1-C or 1-D with the PMB substituent as R$_3$ can be deprotected using a reagent such as TFA/TFMSA, and then reacts with a different R$_3$-L under basic conditions for rapidly synthesizing 1-C or 1-D analogs.

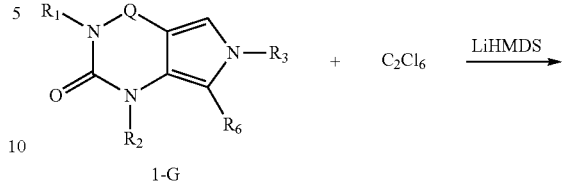

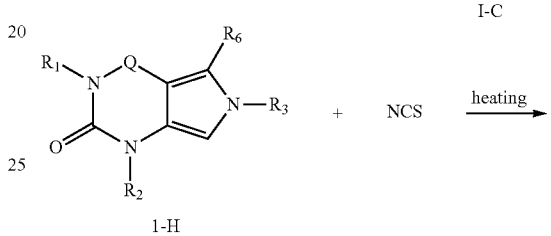

Compounds 1-G and 1-H may be formed by reacting a compound of 1-I and 1-J respectively with for example a R$_3$-L in a solvent such as DMF and a base such as K$_2$CO$_3$ at room temperature or with heating:

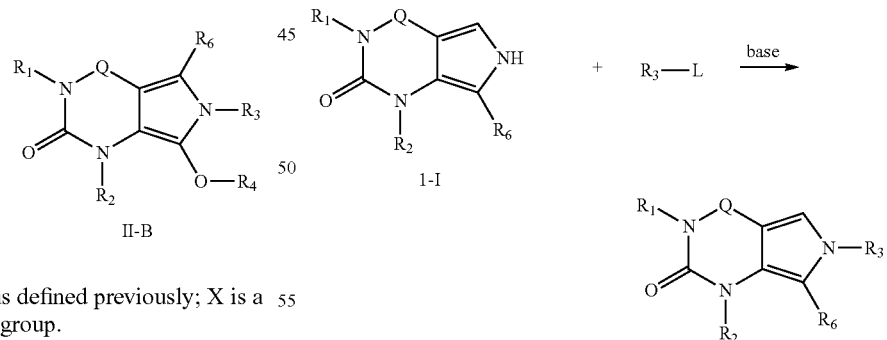

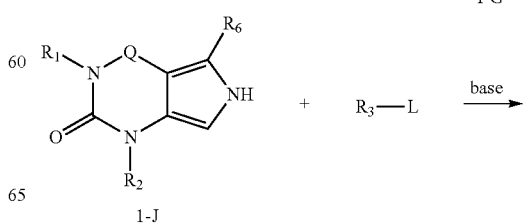

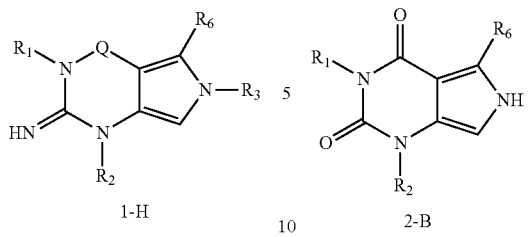

1-H

2-B wherein all the substituents are as defined previously; L is a leaving group such as a halogen group.

(1,3-optionally substituted)-1H-pyrrolo[3,4-d]pyrimidine-2,4(3H,6H)-dione cores, e.g., Intermediate 2 wherein Q is C(=O), may be prepared by reacting (1,3-optionally substituted)-pyrimidine-2,4-dione, e.g., Intermediate 1, e.g., with a strong base such as sodium hydride and a reagent such as TsCHR$_6$NC, e.g., p-toluenesulfonylmethyl isocyanide, in a solvent such as THF. Alternatively, intermediate 1 may react with para-toluenesulfonylmethyl isocyanide to construct the pyrrole ring, and the substituent R$_6$ may introduced at later steps.

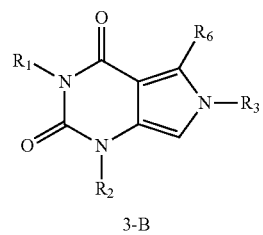

3-B

Compound 4-A and 4-B, wherein X is halo, e.g., Cl, Br or I, may be prepared by halogenating compound 3-A and 3-B. For example, compound 4-A may be formed by reacting Compound 3-A with, e.g., N-chlorosuccinimide (NCS), hexachloroethane, N-bromosuccinimide (NBS), N-iodosuccinimide (NIS) or I$_2$ in a solvent such as THF and a base such as LiHMDS, LDA or BuLi at room or low temperature. Compound 4-B may be prepared by, e.g., reacting compound 3-B with a chlorinating reagent such NCS in a solvent such as CCl$_4$.

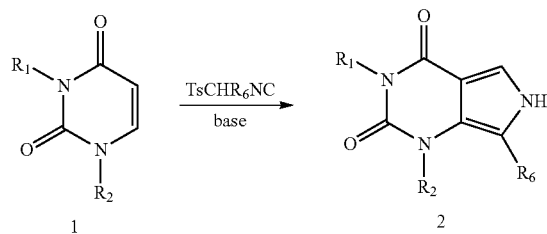

Intermediate 3-A and 3-B may be formed by reacting compound 2-A and 2-B with for example a R$_3$-L in a solvent such as DMF and a base such as K$_2$CO$_3$ or cesium carbonate at room temperature or with heating.

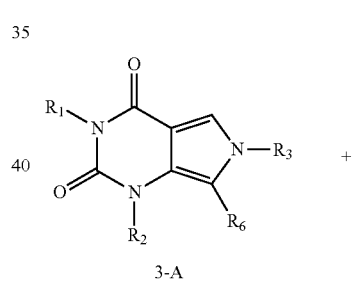

3-A

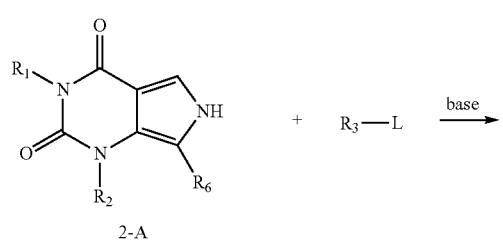

2-A

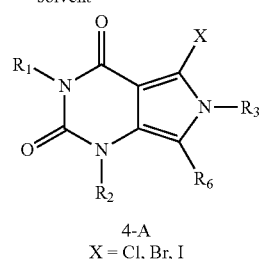

4-A
X = Cl, Br, I

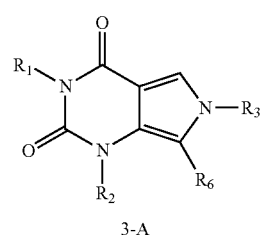

3-A

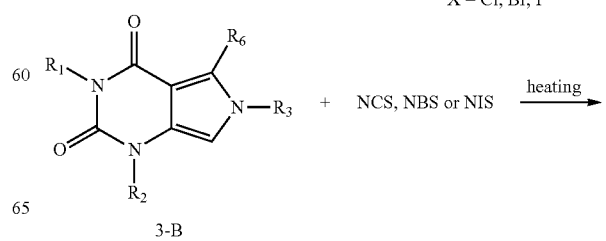

3-B

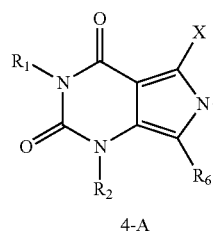

4-B

Compound II-A and II-B wherein Q is C(═O), here Compound 5-A or 5-B, may then be prepared by reacting a compound of 4-A and 4-B respectively with, for example a R₄OH and a base such as potassium carbonate at elevated temperature (e.g., at reflux).

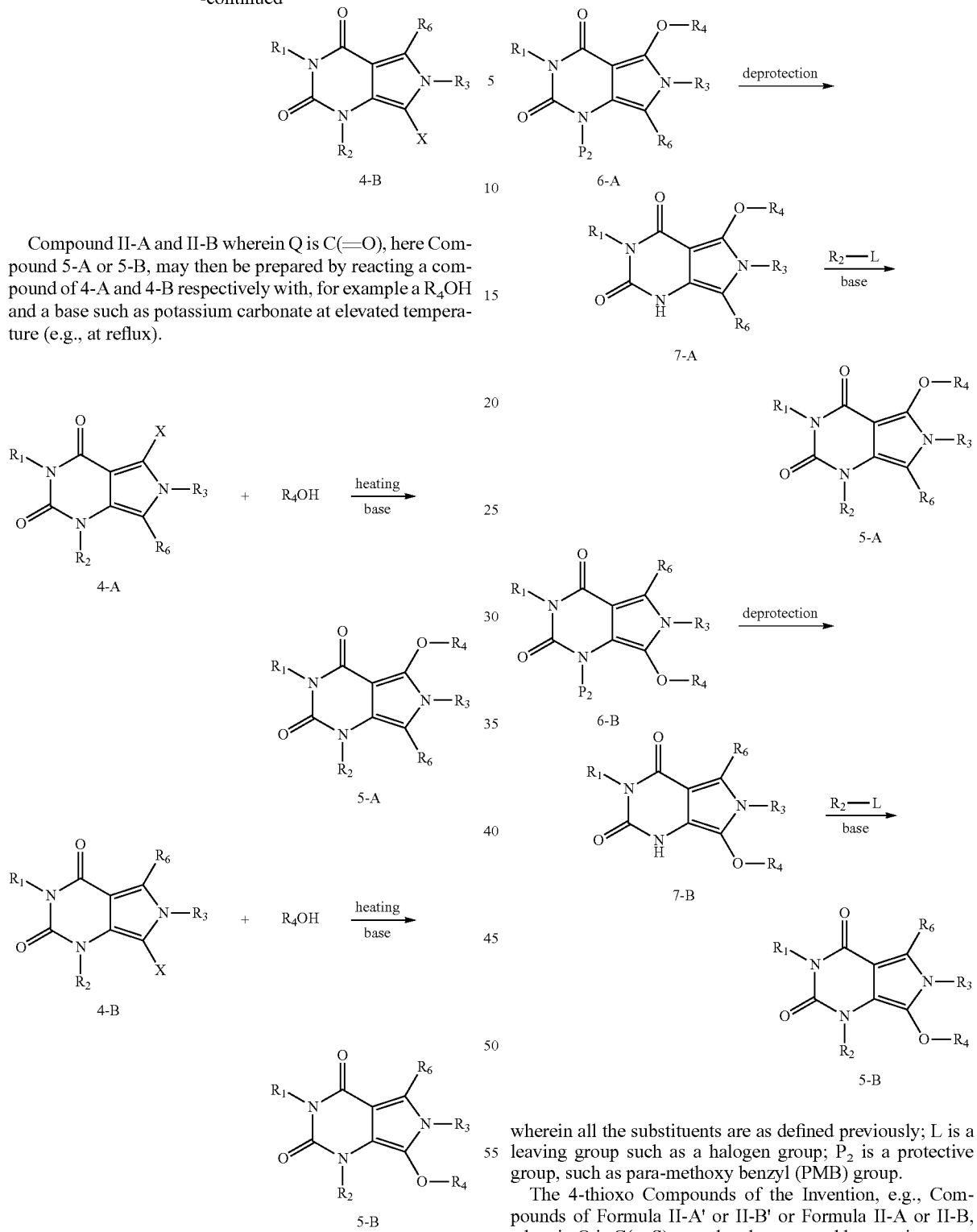

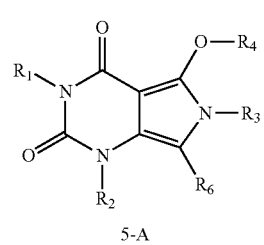

5-A

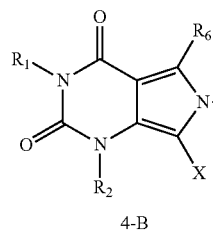

4-B

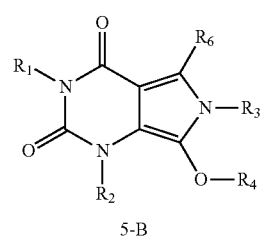

5-B

Compound 5-A or 5-B may also be synthesized from protected intermediate 6-A or 6-B, wherein P₂ is a protective group such as para-methoxy benzyl (PMB) group. After deprotection, the obtained intermediate 7-A or 7-B can react with R₂-L in a solvent such as DMF and a base such as K₂CO₃ at room temperature or with heating to give compound 5-A or 5-B.

wherein all the substituents are as defined previously; L is a leaving group such as a halogen group; P₂ is a protective group, such as para-methoxy benzyl (PMB) group.

The 4-thioxo Compounds of the Invention, e.g., Compounds of Formula II-A' or II-B' or Formula II-A or II-B, wherein Q is C(═S) may then be prepared by reacting compound 5-A or 5-B with P₄S₁₀ in a microwave vial in the presence of a base, e.g., pyridine, and heating the mixture to an elevated temperature, e.g., in a microwave, e.g., to about 150° C. The invention thus provides methods of making a 4-thioxo Compound of the Invention, e.g., Compound of Formula II-A' or II-B' or Formula II-A or II-B, wherein Q of is C(═S) as hereinbefore described, for example, comprising reacting a Compound of Formula II-A' or II-B' or Formula II-A or II-B, respectively, wherein Q is C(=O) with $P_4S_{10}$ in the presence of a base, e.g., pyridine, and heating the reaction mixture to an elevated temperature, e.g., to >50° C., e.g., >100° C., e.g., >150° C., for example, in a microwave to about 150° C.

The 4-imino Compounds of the Invention, e.g., Compounds of Formula II-A' or II-B' or Formula II-A or II-B, wherein Q is C(=N(R_7)) may in turn be converted from the 4-thioxo derivative (i.e., Compounds of Formula II-A' or II-B' or Formula II-A or II-B, wherein with Q is C(=S)) by reacting the 4-thioxo derivative with $NH_2(R_7)$ in the presence of $HgCl_2$, e.g., in a solvent such as THF, and heating the reaction mixture to an elevated temperature, e.g., in a microwave, e.g., to about 110° C. The invention also provides methods of making 4-imino Compounds of the Invention, e.g., Compounds of Formula II-A' or II-B', or Formula II-A or II-B, wherein Q is C(=N(R_7)) as hereinbefore described, for example, comprising reacting a the Compound of Formula II-A' or II-B', or Formula II-A or II-B, respectively wherein Q is C(=S), with $NH_2(R_7)$ in the presence of $HgCl_2$, e.g., in a solvent such as THF, and heating the reaction mixture in a microwave, e.g., to >50° C., e.g., >75° C., e.g., >100° C., for example, in a microwave to about 110° C.

The Compounds of the Invention, e.g., Compounds of Formula II-A' or II-B' or Formula II-A or II-B, wherein Q is $CH_2$ may also be prepared by reacting compound 5-A or 5-B with a reducing agent, e.g., diisobutylaluminum hydride (DIBAL-H), lithium aluminum hydride, sodium borohydride, preferably, DIBAL-H. The invention therefore provides methods of making the Compounds of the Invention, e.g., Compounds of Formula I, wherein Q is $CH_2$ comprising reacting compound 5-A or 5-B with a reducing agent, e.g., diisobutylaluminum hydride (DIBAL-H), lithium aluminum hydride, sodium borohydride, preferably, DIBAL-H.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:
  (i) Neurodegenerative diseases, including Parkinson's disease, restless leg, tremors, dyskinesias, Huntington's disease, Alzheimer's disease, and drug-induced movement disorders;
  (ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;
  (iii) Circulatory and cardiovascular disorders, including cerebrovascular disease, stroke, congestive heart disease, hypertension, pulmonary hypertension, and sexual dysfunction;
  (iv) Respiratory and inflammatory disorders, including asthma, chronic obstructive pulmonary disease, and allergic rhinitis, as well as autoimmune and inflammatory diseases;
  (v) Any disease or condition characterized by low levels of cAMP and/or cGMP (or inhibition of cAMP and/or cGMP signaling pathways) in cells expressing PDE1; and/or
  (vi) Any disease or condition characterized by reduced dopamine D1 receptor signaling activity,
  comprising administering an effective amount of a Compound of the Invention, e.g., a Compound of Formula II-A' or II-B', Formula II-A or II-B, e.g., any of 2.1-2.27, or any of III-A, III-B, IV-A, IV-B, V-A, V-B, VI-A, VI-B, VII-A, VII-B, VIII-A or VIII-B, in free or pharmaceutically acceptable salt form, or a composition comprising the same to a human or animal patient in need thereof.

In an especially preferred embodiment, the invention provides methods of treatment or prophylaxis for narcolepsy. In this embodiment, PDE 1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of
  (i) a PDE 1 Inhibitor of the Invention, e.g., a Compound of Formula II-A' or II-B', Formula II-A or II-B, e.g., any of 2.1-2.27, or any of III-A, III-B, IV-A, IV-B, V-A, V-B, VI-A, VI-B, VII-A, VII-B, VIII-A or VIII-B; and
  (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB),
    in free or pharmaceutically acceptable salt form, to a human or animal patient in need thereof. In another embodiment, the invention provides methods of treatment or prophylaxis for narcolepsy as herein before described, wherein the PDE1 inhibitor is in a form of a pharmaceutical composition.

In another embodiment, the invention further provides methods of treatment or prophylaxis of a condition which may be alleviated by the enhancement of the progesterone signaling comprising administering an effective amount of a Compound of the Invention, in free or pharmaceutically acceptable salt form, to a human or animal patient in need thereof. Disease or condition that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 Inhibitors of the Invention, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors of the Invention may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of
(i) a PDE 1 Inhibitor of the Invention, and
(ii) a hormone, e.g., selected from estrogen and estrogen analogues (e.g., estradiol, estriol, estradiol esters) and progesterone and progesterone analogues (e.g., progestins)
in free or pharmaceutically acceptable salt form, to a human or animal patient in need thereof.

The invention also provides a method for enhancing or potentiating dopamine D1 intracellular signaling activity in a cell or tissue comprising contacting said cell or tissue with an amount of a Compound of the Invention sufficient to inhibit PDE1B activity. The invention further provides a method for enhancing or potentiating dopamine D1 intracellular signaling activity in a cell or tissue comprising contacting said cell or tissue with an amount of a Compound of the Invention as hereinbefore described, in free or salt form, sufficient to inhibit PDE1 activity, e.g., PDE1A or PDE1B activity.

The invention also provides a method for enhancing or potentiating progesterone signaling activity in a cell or tissue comprising contacting said cell or tissue with an amount of a Compound of the Invention sufficient to inhibit PDE1B activity.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention that inhibits PDE1B, wherein PDE1B activity modulates phosphorylation of DARPP-32 and/or the GluR1AMPA receptor.

In another aspect, the invention also provides a method for the treatment for glaucoma or elevated intraocular pressure comprising topical administration of a therapeutically effective amount of a phosphodiesterase type I (PDE1) Inhibitor of the Invention, in free or pharmaceutically acceptable salt form, in an opthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, in free or ophthamalogically acceptable salt form, in combination or association with an ophthamologically acceptable diluent or carrier.

Optionally, the PDE1 Inhibitor of the Invention may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and also may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 Inhibitor of the Invention, in free or pharmaceutically acceptable salt form, such that amount of the agent known to lower intraocular pressure and the amount of the PDE1 Inhibitor of the Invention in combination are effective to treat the condition.

In one embodiment, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 Inhibitor of the Invention. However, methods other than topical administration, such as systemic therapeutic administration, may also be utilized.

The optional additional agent or agents for use in combination with a PDE1 Inhibitor of the Invention may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g.,
1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (parasympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 Inhibitor of the Invention and an agent selected from (i) the prostanoids, unoprostone, latanoprost, travoprost, or bimatoprost; (ii) an alpha adrenergic agonist such as brimonidine, apraclonidine, or dipivefrin and (iii) a muscarinic agonist, such as pilocarpine. For example, the invention provides ophthalmic formulations comprising a PDE-1 Inhibitor of the Invention together with bimatoprost, abrimonidine, brimonidine, timolol, or combinations thereof, in free or ophthamalogically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an $alpha_2$ adrenergic receptor such as brimonidine, for example. For a beta-adrenergic receptor antagonist, one can select an antagonist selective for either $β_1$, or $β_2$, or $β_3$, depending on the appropriate therapeutic application. One can also select a muscarinic agonist selective for a particular receptor subtype such as $M_1$-$M_5$.

The PDE 1 Inhibitor of the Invention may be administered in the form of an ophthalmic composition, which includes an ophthalmic solution, cream or ointment. The ophthalmic composition may additionally include an intraocular-pressure lowering agent.

In yet another example, the PDE-1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, in free or pharmaceutically acceptable salt form, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously administering therapeutically effective amounts of:
 (i) a PDE 1 Inhibitor of the invention, in free or pharmaceutically acceptable salt form; and
 (ii) an antipsychotic, e.g.,
  Typical antipsychotics, e.g.,
   Butyrophenones, e.g. Haloperidol (Haldol, Serenace), Droperidol (Droleptan);
   Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);
   Thioxanthenes, e.g., Chlorprothixene, Flupenthixol (Depixol, Fluanxol), Thiothixene (Navane), Zuclopenthixol (Clopixol, Acuphase);
  Atypical antipsychotics, e.g.,
   Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine,
   in free or pharmaceutically acceptable salt form, to a patient in need thereof.

In a particular embodiment, the Compounds of the Invention are particularly useful for the treatment or prophylaxis of schizophrenia.

Compounds of the Invention, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, in free or pharmaceutically acceptable salt form, to the eye of a patient in need thereof.

In yet another aspect, the invention provides a method for the treatment or prophylaxis of traumatic brain injury comprising administering a therapeutically effective amount of a PDE1 Inhibitor of the Invention, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury. Abnormal calcium homeostasis is believed to be a critical component of the progression of secondary injury in both grey and white matter. For a review of TBI, see Park et al., CMAJ (2008) 178(9):1163-1170, the contents of which are incorporated herein in their entirety. Studies have shown that the cAMP-PKA signaling cascade is down-regulated after TBI and treatment of PDE IV inhibitors such as rolipram to raise or restore cAMP level improves histopathological outcome and decreases inflammation after TBI. As Compounds of the present invention is a PDE1 inhibitor useful for modulating cAMP and/or calcium levels, it is believed that these compounds are also useful for the treatment of TBI, e.g., by restoring cAMP level and/or calcium homeostasis after traumatic brain injury.

The present invention also provides
(i) a Compound of the Invention for use as a pharmaceutical, for example for use in any method or in the treatment of any disease or condition as hereinbefore set forth,
(ii) the use of a Compound of the Invention (in the manufacture of a medicament) for treating any disease or condition as hereinbefore set forth,
(iii) a pharmaceutical composition comprising a Compound of the Invention in combination or association with a pharmaceutically acceptable diluent or carrier, and
(iv) a pharmaceutical composition comprising a Compound of the Invention in combination or association with a pharmaceutically acceptable diluent or carrier for use in the treatment of any disease or condition as hereinbefore set forth.

Therefore, the invention provides use of a Compound of the Invention (for the manufacture of a medicament) for the treatment or prophylactic treatment of the following diseases: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, estrogen-induced endometrial hyperplasia or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling.

The invention also provides use of a Compound of the Invention, in free or pharmaceutically acceptable salt form, (for the manufacture of a medicament) for the treatment or prophylactic treatment of:
a) glaucoma or elevated intraocular pressure,
b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder,
c) traumatic brain injury.

The phrase "Compounds of the Invention" or "PDE 1 inhibitors of the Invention" or "Phosphodiesterase 1 Inhibitor of the Invention" encompasses any and all of the compounds disclosed herewith, e.g., Compound of Formula II, e.g., Formula II-A' or II-B', or Formula II-A or II-B, e.g., any of 2.1-2.27, or any of III-A, III-B, IV-A, IV-B, V-A, V-B, VI-A, VI-B, VII-A, VII-B, VIII-A or VIII-B, in free or (pharmaceutically acceptable) salt form.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "pulmonary hypertension" is intended to encompass pulmonary arterial hypertension.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention are in particular useful for the treatment of Parkinson's disease, narcolepsy and female sexual dysfunction.

Compounds of the Invention may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 Inhibitors of the Invention, e.g., the Compounds of the Invention as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

The synthetic methods for various Compounds of the Present Invention are illustrated below. Other compounds of the Invention and their salts may be made using the methods as similarly described below and/or by methods similar to those generally described in the detailed description and by methods known in the chemical art. The Compounds of the Invention can also be made by using general or specific synthetic methods disclosed in PCT/US2009/06437, the contents of which are hereby incorporated by reference in their entirety

Example 1

6-(4-(1H-1,2,4-triazol-1-yl)benzyl)-1-isobutyl-3-methyl-5-phenoxy-1H-pyrrolo[3,4-d]pyrimidine-2,4(3H,6H)-dione

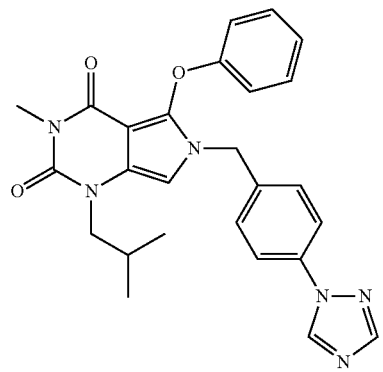 [SMILES: CC(C)Cn1c(=O)n(C)c(=O)c2c(Oc3ccccc3)n(Cc3ccc(-n4cncn4)cc3)cc21]

Step 1: 1-isobutyl-3-methylpyrimidine-2,4(1H,3H)-dione

A suspension of 3-Methyluracil (3.0 g, 23.8 mmol), isobutyl iodide (7 mL, 60 mmol) and cesium carbonate (11.6 g, 35.7 mmol) in DMF (30 mL) is stirred at room temperature over a weekend. Solvent is removed under vacuum. The residue is treated with water, and then extracted with dichloromethane four times. The combined organic phase is washed with brine, dried over anhydrous sodium sulfate, and then filtered through a short silica gel column. The filtrate is concentrated to dryness to give product as off white solids, which is used in the next step without further purification. MS (ESI) m/z 183.1 [M+H]$^+$.

Step 2: 1-isobutyl-3-methyl-1H-pyrrolo[3,4-d]pyrimidine-2,4(3H,6H)-dione

Sodium hydride (95%, 1.74 g, 69 mmol) is suspended in 20 mL of anhydrous THF, and then a mixture of 1-isobutyl-3-methylpyrimidine-2,4(1H,3H)-dione (approx. 23 mmol) and p-toluenesulfonylmethyl isocyanide (97%, 7.0 g, 35 mmol) in 20 mL of anhydrous THF is added dropwise over 80 minutes at 0° C. The mixture is stirred at room temperature for an hour after the completion of the addition, and then carefully quenched with water. The mixture is diluted with 50 mL of saturated NaHCO$_3$, and then extracted with CH$_2$Cl$_2$ five times. The combined organic phase is washed with brine, and then dried with anhydrous Na$_2$SO$_4$. After filtration, the filtrate is evaporated to dryness under reduced pressure to give product as light brown solids, which is used in the next step without further purification. MS (ESI) m/z 222.2 [M+H]$^+$.

Step 3: 1-isobutyl-6-(4-methoxybenzyl)-3-methyl-1H-pyrrolo[3,4-d]pyrimidine-2,4(3H,6H)-dione A suspension of 1-isobutyl-3-methyl-1H-pyrrolo[3,4-d]pyrimidine-2,4(3H,6H)-dione (1.8 g, 8.3 mmol), 1-(chloromethyl)-4-methoxybenzene (1.3 mL, 9.9 mmol) and potassium carbonate (1.7 g, 12 mmol) in anhydrous DMF is stirred at room temperature overnight. The mixture is diluted with 100 mL of water, and then extracted with CH$_2$Cl$_2$ three times. The combined organic phase is washed with brine, and then dried with anhydrous Na$_2$SO$_4$. After filtration, the filtrate is concentrated under vacuum. The residue is purified by silica gel chromatography to give product as pale yellow solids. MS (ESI) m/z 342.2 [M+H]$^+$.

Step 4: 5-chloro-1-isobutyl-6-(4-methoxybenzyl)-3-methyl-1H-pyrrolo[3,4-d]pyrimidine-2,4(3H,6H)-dione 1-isobutyl-6-(4-methoxybenzyl)-3-methyl-1H-pyrrolo[3,4-d]pyrimidine-2,4(3H,6H)-dione (1.88 g, 5.5 mmol) and hexachloroethane (6.5 g, 26.5 mmol) are dissolved in anhydrous THF (3 mL), and then 1.0 M LiHMDS in THF (11 mL, 11 mmol) is added dropwise over 2 hours. The reaction mixture is stirred at room temperature for an hour, and then quenched with saturated ammonium chloride aqueous solution. The mixture is poured into cold water (100 mL), and then extracted with ethyl acetate three times. The combined organic phase is dried with anhydrous sodium sulfate. After filtration, the filtrate is evaporated to dryness to give 2.5 g of crude product as light brown solids, which is used in the next step without further purification. MS (ESI) m/z 376.1 [M+H]$^+$.

Step 5: 5-chloro-1-isobutyl-3-methyl-1H-pyrrolo[3,4-d]pyrimidine-2,4(3H,6H)-dione Crude 5-chloro-1-isobutyl-6-(4-methoxybenzyl)-3-methyl-1H-pyrrolo[3,4-d]pyrimidine-2,4(3H,6H)-dione (2.5 g) is dissolved in 5 mL of methylene chloride containing TFA (2 mL) and TFMSA (1.6 mL). The reaction mixture is stirred at room temperature overnight. After routine workup, the obtained crude product is purified by column chromatography to give 730 mg of product as gray solids. MS (ESI) m/z 256.1 [M+H]$^+$.

Step 6: 6-(4-(1H-1,2,4-triazol-1-yl)benzyl)-5-chloro-1-isobutyl-3-methyl-1H-pyrrolo[3,4-d]pyrimidine-2,4(3H,6H)-dione A suspension of 5-chloro-1-isobutyl-3-methyl-1H-pyrrolo[3,4-d]pyrimidine-2,4(3H,6H)-dione (103 mg, 0.4 mmol), 1-(4-(bromomethyl)phenyl)-1H-1,2,4-triazole (93 mg, 0.48 mmol) and cesium carbonate (195 mg, 0.6 mmol) in anhydrous DMF (3 mL) is stirred at room temperature for 3 hours. The mixture is diluted with 20 mL of saturated sodium bicarbonate, and then extracted with CH$_2$Cl$_2$ three times. The combined organic phase is washed with brine, and then dried with anhydrous Na$_2$SO$_4$. After filtration through celite, the filtrate is concentrated to dryness under vacuum to give 160 mg of crude product as light brown solids, which is used in the next step without further purification. MS (ESI) m/z 413.2 [M+H]$^+$.

Step 7: 6-(4-(1H-1,2,4-triazol-1-yl)benzyl)-1-isobutyl-3-methyl-5-phenoxy-1H-pyrrolo[3,4-d]pyrimidine-2,4(3H,6H)-dione Crude 6-(4-(1H-1,2,4-triazol-1-yl)benzyl)-5-chloro-1-isobutyl-3-methyl-1H-pyrrolo[3,4-d]pyrimidine-2,4(3H,6H)-dione (12 mg, 0.029 mmol), phenol (14 mg, 0.15 mmol) and Cs$_2$CO$_3$ (29 mg, 0.087 mmol) are placed in a microwave vial, and then dioxane (0.25 mL) is added. The vial is sealed and heated in a Biotage microwave instrument at 150° C. for 3 h. The reaction mixture is then purified with a semi-preparative HPLC to give 8.0 mg of product as off-white solid (purity: 97%). MS (ESI) m/z 471.2 [M+H]+.

Example 2

6-(4-(1H-1,2,4-triazol-1-yl)benzyl)-5-(4-fluorophenoxy)-1-isobutyl-3-methyl-1H-pyrrolo[3,4-d]pyrimidine-2,4(3H,6H)-dione

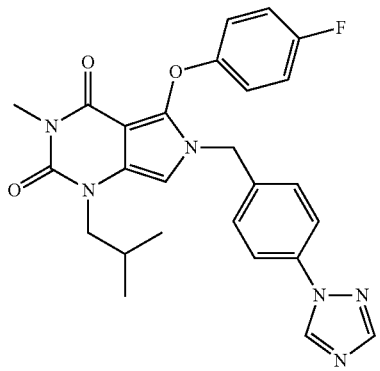 [SMILES: CC(C)Cn1c(=O)n(C)c(=O)c2c(Oc3ccc(F)cc3)n(Cc3ccc(-n4cncn4)cc3)cc21]

The synthetic procedure of this compound is analogous to EXAMPLE 1 wherein 4-fluorophenol is used in step 7 instead of phenol. MS (ESI) m/z 489.2 [M+H]+.

Example 3

6-(4-(1H-imidazol-1-yl)benzyl)-5-(4-fluorophenoxy)-1-isobutyl-3-methyl-1H-pyrrolo[3,4-d]pyrimidine-2,4(3H,6H)-dione

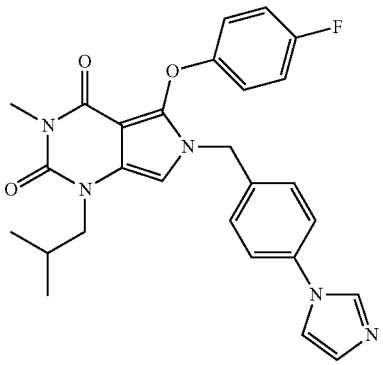 [SMILES: CC(C)Cn1c(=O)n(C)c(=O)c2c(Oc3ccc(F)cc3)n(Cc3ccc(-n4ccnc4)cc3)cc21]

The synthetic procedure of this compound is analogous to EXAMPLE 1 wherein 1-(4-(chloromethyl)phenyl)-1H-imidazole is added in step 6 instead of 1-(4-(bromomethyl)phenyl)-1H-1,2,4-triazole; and 4-fluorophenol is used in step 7 instead of phenol. MS (ESI) m/z 488.2 [M+H]+.

Example 4

1-isobutyl-6-(4-methoxybenzyl)-3,7-dimethyl-5-phenoxy-1H-pyrrolo[3,4-d]pyrimidine-2,4(3H,6H)-dione

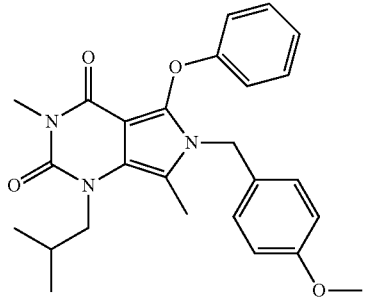

Step 1: 1-isobutyl-3,7-dimethyl-1H-pyrrolo[3,4-d]pyrimidine-2,4(3H,6H)-dione

Sodium hydride (95%, 116 mg, 4.6 mmol) is suspended in 10 mL of anhydrous THF, and then a mixture of 1-isobutyl-3-methylpyrimidine-2,4(1H,3H)-dione (300 mg, 1.65 mmol) and 1-(p-toluenesulfonyl)-ethyl isocyanide (413 mg, 1.98 mmol) in 5 mL of anhydrous THF is added dropwise over 1 h at 0° C. The mixture is stirred at room temperature for 3 h at room temperature after the completion of the addition, and then carefully quenched with water. The mixture is diluted with saturated NaHCO$_3$, and then extracted with CH$_2$Cl$_2$ five times. The combined organic phase is washed with brine, and then dried with anhydrous Na$_2$SO$_4$. After filtration, the filtrate is evaporated to dryness under reduced pressure, and the residue is purified by basic alumina column chromatography to give 247 mg of product (yield: 64%). MS (ESI) m/z 236.1 [M+H]+.

Step 2: 1-isobutyl-6-(4-methoxybenzyl)-3,7-dimethyl-1H-pyrrolo[3,4-d]pyrimidine-2,4(3H,6H)-dione A suspension of 1-isobutyl-3,7-dimethyl-1H-pyrrolo[3,4-d]pyrimidine-2,4(3H,6H)-dione (78 mg, 0.33 mmol), 1-(chloromethyl)-4-methoxybenzene (88 μL, 0.63 mmol) and cesium carbonate (344 mg, 1.06 mmol) in anhydrous DMF is stirred at room temperature overnight. The mixture is diluted with 30 mL of water, and then extracted with CH$_2$Cl$_2$ three times. The combined organic phase is washed with brine, and then dried with anhydrous Na$_2$SO$_4$. After filtration, the filtrate is concentrated under vacuum. The residue is purified by basic alumina column chromatography to give 110 mg of product (yield: 93%). MS (ESI) m/z 356.2 [M+H]+.

Step 3: 5-chloro-1-isobutyl-6-(4-methoxybenzyl)-3,7-dimethyl-1H-pyrrolo[3,4-d]pyrimidine-2,4(3H,6H)-dione 1-isobutyl-6-(4-methoxybenzyl)-3,7-dimethyl-1H-pyrrolo[3,4-d]pyrimidine-2,4(3H,6H)-dione (103 mg, 0.29 mmol) and hexachloroethane (400 mg, 1.7 mmol) are dissolved in anhydrous THF, and then 1.0M LiHMDS in THF (1.4 mL, 1.4 mmol) is added dropwise. The reaction mixture is stirred at room temperature for an hour, and then quenched with saturated ammonium chloride aqueous solution. The mixture is purified by silica-gel column chromatography to give pure product as off-white solids (yield: 64%). MS (ESI) m/z 390.2 [M+H]+.

Step 4: 1-isobutyl-6-(4-methoxybenzyl)-3,7-dimethyl-5-phenoxy-1H-pyrrolo[3,4-d]pyrimidine-2,4(3H,6H)-dione 5-chloro-1-isobutyl-6-(4-methoxybenzyl)-3,7-dimethyl-1H-pyrrolo[3,4-d]pyrimidine-2,4(3H,6H)-dione (20 mg, 0.051 mmol) is placed in a Biotage microwave vial, and then phenol (24 mg, 0.25 mmol) and cesium carbonate (50 mg, 0.15 mmol) are added. The mixture is heated at 160° C. in a Biotage microwave instrument for 2 h., and then purified by a semi-preparative HPLC to give 17 mg of pure product as off-white solids. MS (ESI) m/z 448.2 [M+H]$^+$.

Example 5

1-isobutyl-3-methyl-5-phenoxy-6-(4-(pyridin-2-yl)benzyl)-1H-pyrrolo[3,4-d]pyrimidine-2,4(3H,6H)-dione

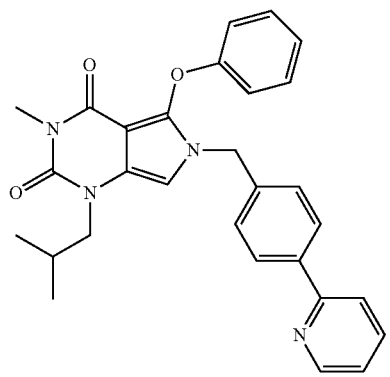 [SMILES: CC(C)Cn1c(=O)n(C)c(=O)c2c(Oc3ccccc3)n(Cc3ccc(-c4ccccn4)cc3)cc21]

The synthetic procedure of this compound is analogous to EXAMPLE 1 wherein 2-(4-(chloromethyl)phenyl)pyridine is added in step 6 instead of 1-(4-(bromomethyl)phenyl)-1H-1,2,4-triazole. MS (ESI) m/z 481.2 [M+H]$^+$.

Example 6

6-(4-(1H-1,2,4-triazol-1-yl)benzyl)-5-(cyclopentyloxy)-1-isobutyl-3-methyl-1H-pyrrolo[3,4-d]pyrimidine-2,4(3H,6H)-dione

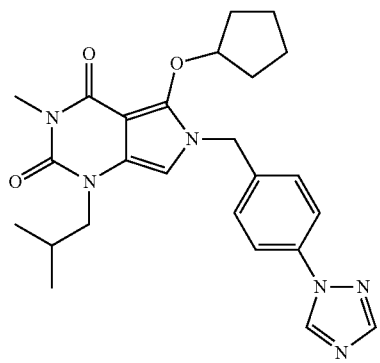 [SMILES: CC(C)Cn1c(=O)n(C)c(=O)c2c(OC3CCCC3)n(Cc3ccc(-n4cncn4)cc3)cc21]

The synthetic procedure of this compound is analogous to EXAMPLE 1 wherein cyclopentanol is used in step 7 instead of phenol. MS (ESI) m/z 463.2 [M+H]$^+$.

Example 7

Measurement of PDE1B Inhibition in vitro Using IMAP Phosphodiesterase Assay Kit

Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp) Inhibition of phosphodiesterase, therefore, is detected as a decrease in Δmp.

Enzyme assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM CaCl$_2$, 10 U/ml of calmodulin (Sigma P2277), 10 mM Tris-HCl pH 7.2, 10 mM MgCl$_2$, 0.1% BSA, 0.05% NaN$_3$) to yield a final concentration of 1.25 mU/ml. 99 μl of diluted enzyme solution is added into each well in a flat bottom 96-well polystyrene plate to which 1 μl of test compound dissolved in 100% DMSO is added. Selected Compounds of the Invention are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased ΔmP, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus ΔmP, which allows $IC_{50}$ values to be estimated using nonlinear regression software (XLFit; IDBS, Cambridge, Mass.).

The Compounds of the Invention are selected and tested in this assay to show PDE1 inhibitory activity, e.g., Examples 1-7 are shown to have an $IC_{50}$ of less than 25 μm, some less than 1 μm, some less than 200 nM, some less than 50 nM, some less than 5 nM.

Example 8

PDE1 Inhibitor Effect on Sexual Response in Female Rats

The effect of PDE1 inhibitors on Lordosis Response in female rats may be measured as described in Mani, et al., Science (2000) 287: 1053. Ovariectomized and cannulated wild-type rats are primed with 2 μg estrogen followed 24 hours later by intracerebroventricular (icv) injection of progesterone (2 μg), PDE1 inhibitors of the present invention (0.1 mg, 1.0 mg or 2.5 mg) or sesame oil vehicle (control). The rats may be tested for lordosis response in the presence of male rats. Lordosis response may be quantified by the lordosis quotient (LQ=number of lordosis/10 mounts×100). The LQ for estrogen-primed female rats receiving Compounds of the Invention, at 0.1 mg, will likely be similar to estrogen-primed rats receiving progesterone and higher than for estrogen-primed rats receiving vehicle.

What is claimed is:

1. A Compound of Formula II-A' or II-B':

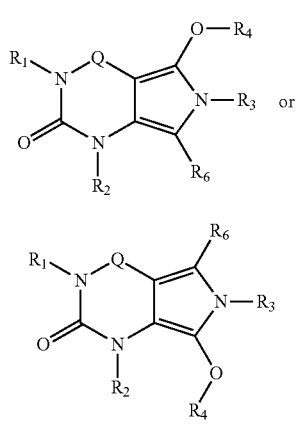

wherein
(i) Q is —C(=S)—, —C(=O)—,
(ii) $R_1$ is H or $C_{1-6}$alkyl;
(iii) $R_2$ is H, or $C_{1-6}$alkyl wherein said alkyl group is optionally substituted with halo or hydroxy;
(iv) $R_3$ is attached to the nitrogen on the pyrrolo portion of Formula II-A' or II-B' and is a moiety of Formula A

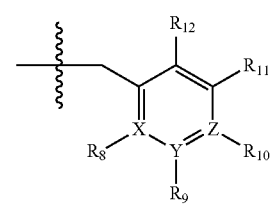

wherein X, Y and Z are, independently, N or C, and $R_8$, $R_9$, $R_{11}$ and
$R_{12}$ are independently H or halogen; and $R_{10}$ is
$C_{1-6}$alkoxy,
$C_{3-8}$cycloalkyl,
hetero$C_{3-8}$cycloalkyl,
halo$C_{1-6}$alkyl,
aryl,
heteroaryl,
wherein the aryl, heteroaryl, cycloalkyl or heterocycloalkyl is optionally substituted with one or more $C_{1-6}$alkyl, halogen, halo$C_{1-6}$alkyl, hydroxy, carboxy, —SH, or an additional aryl or heteroaryl;
provided that when X, Y or Z is nitrogen, $R_8$, $R_9$ or $R_{10}$, respectively, is not present;
(v) $R_4$ is:
$C_{3-7}$cycloalkyl,
aryl,
$C_{3-7}$cycloalkyl,
heteroaryl, or
aryl$C_{1-4}$alkyl,
wherein the aryl or heteroaryl is optionally substituted with one or more group selected from halo, hydroxy, $C_{1-6}$alkyl, $C_{1-6}$alkoxy and $C_{3-8}$cycloalkyl,
(vi) $R_6$ is H, $C_{1-6}$alkyl;
in free or salt form.

2. The Compound according to claim 1, wherein said compound is selected from any one of the following:
A) a Compound of formula IV-A or IV-B:

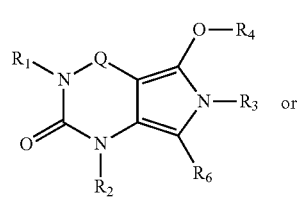

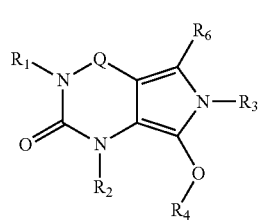

wherein:
(i) Q is —C(=S)—, —C(=O)—;
(ii) $R_1$ is H or $C_{1-6}$alkyl;
(iii) $R_2$ is
$C_{1-6}$alkyl wherein said alkyl group is optionally substituted with halo or hydroxy,
(iv) $R_3$ is attached to the nitrogen on the pyrrolo portion of Formula IV-A or IV-B and is a moiety of Formula A

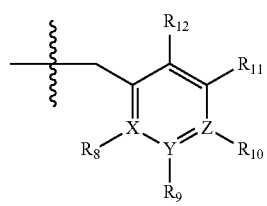

Formula A wherein X, Y and Z are, independently, N or C, and $R_8$, $R_9$, $R_{11}$ and $R_{12}$ are independently H or halogen; and $R_{10}$ is $C_{1-6}$alkoxy, $C_{3-8}$cycloalkyl, hetero$C_{3-8}$cycloalkyl, aryl, heteroaryl, wherein the aryl, heteroaryl, cycloalkyl or heterocycloalkyl is optionally substituted with one or more $C_{1-6}$alkyl, halogen, halo$C_{1-6}$alkyl, hydroxy, carboxy, —SH, or an additional aryl or heteroaryl;

provided that when X, Y or X is nitrogen, $R_8$, $R_9$ or $R_{10}$, respectively, is not present;

(v) $R_4$ is $C_{3-7}$cycloalkyl, aryl, heteroaryl, or aryl$C_{1-4}$alkyl, wherein the aryl or heteroaryl is optionally substituted with one or more group selected from halo, hydroxy, $C_{1-6}$alkyl, $C_{1-6}$alkoxy and $C_{3-8}$cycloalkyl, (vi) $R_6$ is H, $C_{1-6}$alkyl;

in free or salt form;

B) a Compound of formula V-A or V-B:

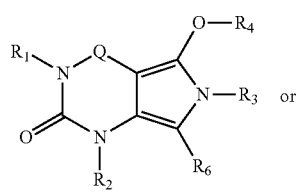

Formula V-A

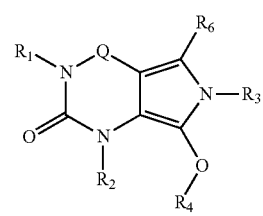

Formula V-B wherein:

(i) Q is —C(=O)—;

(ii) $R_1$ is H or $C_{1-6}$alkyl;

(iii) $R_2$ is $C_{1-6}$alkyl;

(iv) $R_3$ is attached to the nitrogen on the pyrrolo portion of Formula V-A or V-B and is a moiety of Formula A

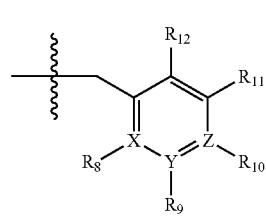

Formula A wherein X, Y and Z are, independently, N or C, and $R_8$, $R_9$, $R_{11}$ and $R_{12}$ are independently H or halogen; and $R_{10}$ is selected from methoxy, pyridyl, 6-fluoropyrid-2-yl, diazolyl, triazolyl, 1-methylpyrroldin-2-yl;

provided that when X, Y or Z is nitrogen, $R_8$, $R_9$ or $R_{10}$, respectively, is not present;

(v) $R_4$ is $C_{3-7}$cycloalkyl, aryl, heteroaryl, or aryl$C_{1-4}$alkyl, wherein the aryl or heteroaryl is optionally substituted with one or more group selected from halo, hydroxy, $C_{1-6}$alkyl, $C_{1-6}$alkoxy and $C_{3-8}$cycloalkyl, (vi) $R_6$ is H, $C_{1-6}$alkyl, in free or salt form;

C) a Compound of formula VI-A or VI-B:

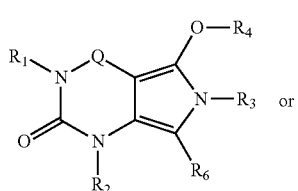

Formula VI-A

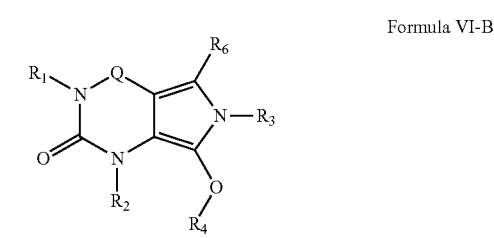

Formula VI-B wherein:

(i) Q is —C(=O)—;

(ii) $R_1$ is H or $C_{1-6}$alkyl;

(iii) $R_2$ is $C_{1-6}$alkyl;

(iv) $R_3$ is attached to the nitrogen on the pyrrolo portion of Formula VI-A or VI-B and is a moiety of Formula A

47

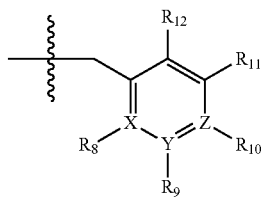
Formula A wherein X, Y and Z are, independently, N or C, and $R_8$, $R_9$, $R_{11}$ and $R_{12}$ are independently H or halogen; and $R_{10}$ is selected from methoxy, pyridyl, 6-fluoropyrid-2-yl, diazolyl, triazolyl, 1-methylpyrroldin-2-yl;

provided that when X, Y or Z is nitrogen, $R_8$, $R_9$ or $R_{10}$, respectively, is not present;

(v) $R_4$ is
aryl optionally substituted with one or more group selected from halo, hydroxy, $C_{1-6}$alkyl, $C_{1-6}$alkoxy and $C_{3-8}$cycloalkyl, (vi) $R_6$ is H, in free or salt form;

D) a Compound of formula VII-A or VII-B:

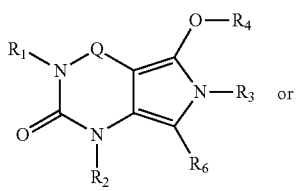

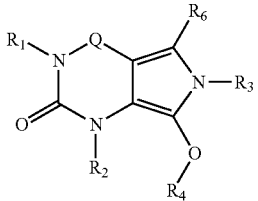

wherein
Q is —C(=O)—;
$R_1$ is H or $C_{1-6}$alkyl;
$R_2$ is $C_{1-6}$alkyl;
$R_3$ is:
attached to the nitrogen on the pyrrolo portion of Formulae VILA or VII-B and is a moiety of Formula A

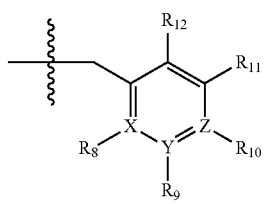
Formula A wherein X, Y and Z are C; $R_8$, $R_9$, $R_{11}$ and $R_{12}$ are H; and $R_{10}$ is $C_{1-6}$alkoxy or heteroaryl;

48

$R_4$ is:
$C_{3-7}$cycloalkyl,
aryl optionally substituted with one or more group selected from halo, hydroxy, $C_{1-6}$alkyl, $C_{1-6}$alkoxy and $C_{3-8}$cycloalkyl,
$R_6$ is H or $C_{1-6}$alkyl, in free or salt form;

E) a Compound of Formula VIII-A or VIII-B:

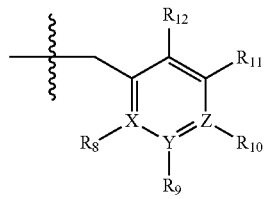

Q is —C(=O)—;
$R_1$ is H or $C_{1-6}$alkyl;
$R_2$ is $C_{1-6}$alkyl;
$R_3$ is:
a moiety of Formula A Formula A wherein X, Y and Z are C; $R_8$, $R_9$, $R_{11}$ and $R_{12}$ are H; and $R_{10}$ is $C_{1-6}$alkoxy or heteroaryl;

$R_4$ is aryl optionally substituted with one or more halo; and $R_6$ is H or $C_{h6}$alkyl, in free or salt form.

3. The compound according to claim 1, wherein $R_{10}$ is selected from 5-fluoropyrid-2-yl, 4-fluoropyrid-2-yl, 3-fluoropyrid-2-yl, 1-methylpyrrolidin-3-yl, 1-methylpyrrolidin-2-yl, 1-ethylpiperidin-1-yl or 1-methylpiperidin-2-yl, in free or salt form.

4. The compound according to claim 1, wherein said compound is selected from any of the following:

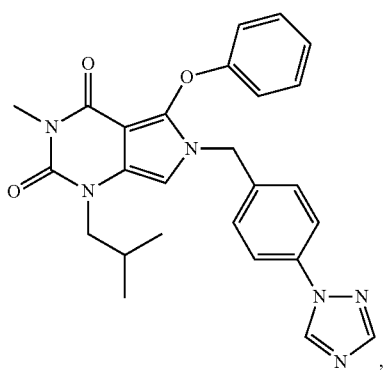

,

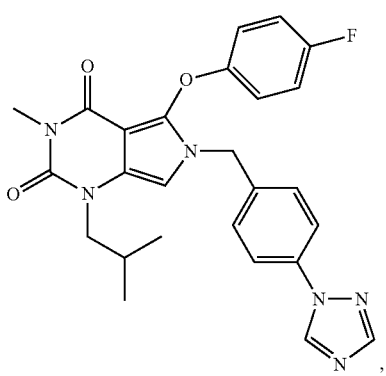

,

,

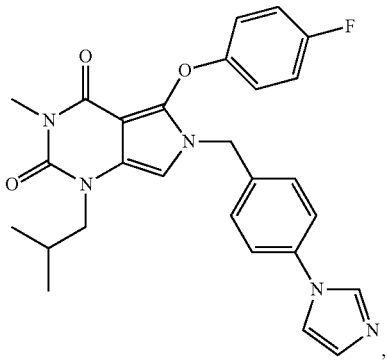

,

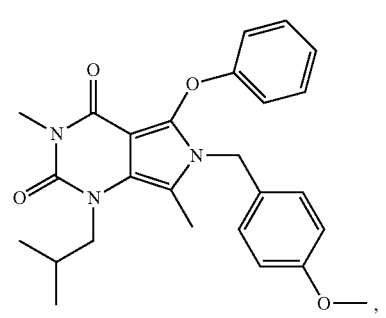

,

-continued

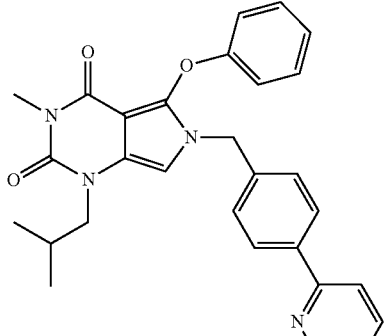

and

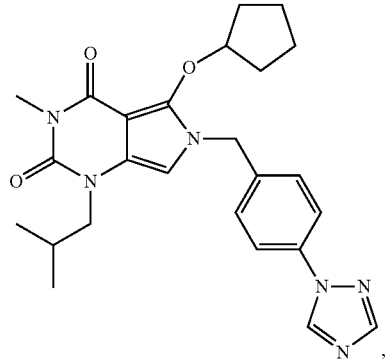

, in free or salt form.

5. The compound according to claim 1, wherein said compound is:

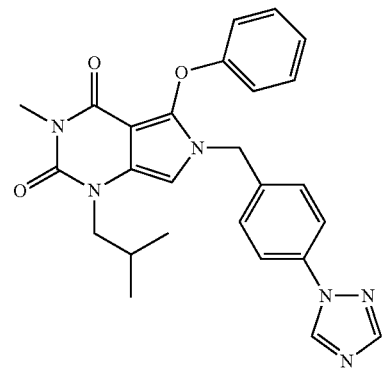 [SMILES: CC(C)Cn1c(=O)n(C)c(=O)c2c(Oc3ccccc3)n(Cc3ccc(-n4cncn4)cc3)cc21]

in free or salt form.

6. A pharmaceutical composition comprising a compound according to claim 1, in free or pharmaceutically acceptable salt form, in admixture with a pharmaceutically acceptable diluent or carrier.

7. A method of treating any of the following conditions: Parkinson's disease, restless leg, tremors, dyskinesias, Huntington's disease, Alzheimer's disease, and drug-induced movement disorders; depression, attention deficit disorder, attention deficit hyperactivity disorder, bipolar illness, anxiety, sleep disorder, narcolepsy, cognitive impairment, dementia, Tourette's syndrome, autism, fragile X syndrome, psychostimulant withdrawal, and/or drug addiction; cerebrovascular disease, stroke, congestive heart disease, hypertension, pulmonary hypertension, and/or sexual dysfunction; asthma, chronic obstructive pulmonary disease, and/or allergic rhinitis, and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, estrogen-induced endometrial hyperplasia or carcinoma; comprising administering a therapeutically effective amount of a compound according to claim 1, in free or pharmaceutically acceptable salt form, to a patient in need of such treatment.

8. The method of claim 7, wherein the condition is Parkinson's disease.

9. The method of claim 7, wherein the condition is cognitive impairment.

10. The method of claim 7, wherein the condition is narcolepsy.

11. The method of claim 10 further comprising administering a compound or compounds selected from central nervous system stimulants, modafinil, antidepressants, and gamma hydroxybutyrate, to a patient in need thereof.

12. The method of claim 7, wherein said condition is female sexual dysfunction.

13. The method of claim 12, further comprising administering a compound or compounds selected from a group consisting of estradiol, estriol, estradiol esters, progesterone and progestins to a patient in need thereof.

14. A method for the treatment of treatment for glaucoma or elevated intraocular pressure comprising topical administration of a therapeutically effective amount of a compound according to claim 1, in free or pharmaceutically acceptable salt form, in an opthalmically compatible carrier to the eye of a patient in need thereof.

15. A method for the treatment of psychosis, schizophrenia, schizoaffective disorder, schizophreniform disorder, psychotic disorder, delusional disorder, and mania, such as in acute manic episodes and bipolar disorder, comprising administering a therapeutically effective amount of a compound according to claim 1, in free or pharmaceutically acceptable salt form, to a patient in need thereof.

16. A method for the treatment of traumatic brain injury comprising administering to a patient in need thereof, a compound according to claim 1, in free or pharmaceutically acceptable salt form.

17. A method for lengthening or enhancing growth of the eyelashes by administering an effective amount of a prostaglandin analogue, concomitantly, simultaneously or sequentially with an effective amount of a compound according to claim 1, in free or pharmaceutically acceptable salt form.

* * * * *